United States Patent [19]

Terao et al.

[11] Patent Number: 4,563,446

[45] Date of Patent: Jan. 7, 1986

[54] THROMBOXANE SYNTHETASE INHIBITING 3-(1-ALKENYL) PYRIDINES

[75] Inventors: Shinji Terao, Osaka; Kohei Nishikawa, Kyoto, both of Japan

[73] Assignee: Takeda Chemical Industries, Ltd., Osaka, Japan

[21] Appl. No.: 632,332

[22] Filed: Jul. 19, 1984

[30] Foreign Application Priority Data

Jul. 27, 1983 [JP] Japan ................................ 58-138585
Nov. 4, 1983 [JP] Japan ................................ 58-207759

[51] Int. Cl.[4] .................. C07D 213/89; C07D 213/59; C07D 213/24; A61K 31/44
[52] U.S. Cl. ...................................... 514/63; 514/277; 514/332; 514/333; 514/336; 514/338; 514/340; 514/341; 514/357; 514/358; 546/256; 546/263; 546/270; 546/276; 546/278; 546/284; 546/330; 546/331; 546/333; 546/340; 546/342; 546/343; 546/346; 546/350; 546/14
[58] Field of Search ............... 546/350, 284, 283, 256, 546/266, 267, 255, 274, 268, 333, 340, 278, 275, 279, 281, 346, 343, 330, 342, 263, 331, 270, 276, 14; 514/277, 332, 333, 336, 338, 340, 341, 357, 358, 63

[56] References Cited

PUBLICATIONS

Chemical Abstracts 100:174676y, (1984).
Chemical Abstracts 95:180667r, (1981).
J. Med. Chem. 24 1139—Iizuka—Highly Selective Inhibitors of Thromboxane Synthetase. 1. Imidazole Derivatives.
J. Med. Chem. 24 1149—Tanouchi—Highly Selective Inhibitors of Thromboxane Synthetase. 2. Pyridine Derivatives.

Primary Examiner—Henry R. Jiles
Assistant Examiner—Dale A. Bjorkman
Attorney, Agent, or Firm—Wegner & Bretschneider

[57] ABSTRACT

Novel compounds of the formula:

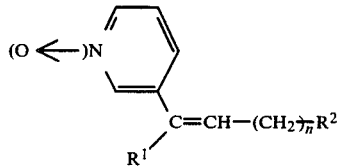

wherein $R^2$ is an aromatic or heterocyclic group, which may optionally be substituted, $R^2$ is a methyl group, a hydroxymethyl group, a nitroxymethyl group, a formyl group, a nitrogen-containing five-membered ring-methyl group, an acetal-methyl group, a trialkylsilyloxymethyl group, an alkyl- or aryl-sulfonyloxymethyl group, an alkyl- or aryl-sulfonylaminocarbonyloxymethyl group, an acyloxymethyl group, an alkoxycarbonyloxymethyl group, a halogenomethyl group, an alkoxymethyl group, an aryloxymethyl group, a cyano group, a carbamoyl group which may optionally be substituted, a carbamoyloxymethyl group which may optionally be substituted, a thiocarbamoyloxymethyl group which may optionally be substituted, and an alkoxycarbonyl group, n is an integer of 1 to 20, and

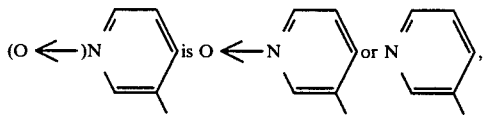

provided that n is an integer of 9 to 20 when

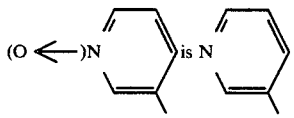

and, at the same time, $R^2$ is a carboxyl group or an alkoxycarbonyl group, or a pharmacologically acceptable salt thereof, have a selective inhibitory action on biosynthesis of thromboxane $A_2(TXA_2)$ and an effect of enhancing the production of prostaglandin $I_2(PGI_2)$, and can be used for mammals to prevent and treat arterial thrombosis caused by platelet aggregation or ischemic diseases caused by vasospasms in cardiac, cerebral and peripheral circulatory system (e.g. cardiac infarction, stroke, occlusion of blood vessels in kidney, lung and other organs, pectic ulcer, etc.).

11 Claims, No Drawings

THROMBOXANE SYNTHETASE INHIBITING 3-(1-ALKENYL) PYRIDINES

This invention relates to novel substituted vinyl derivatives which are capable of inhibiting thromboxane A$_2$ (TXA$_2$) synthetase specifically.

TXA$_2$ is one of the arachidonic acid metabolites and is a potent inducer of platelet aggregation and vascular smooth muscle contractions. Therefore, when produced in excess in vivo, TXA$_2$ causes platelet aggregation, vascular occlusion and vasospasm and thus may be a risk factor of ischemic heart, kidney and brain diseases. The present inventors synthesized a variety of compounds in search of substance having TXA$_2$ synthetase inhibiting activity and, as a result, found a new class of compounds having excellent TXA$_2$ synthetase inhibiting activity.

Thus, the invention provides:

(1) A compound of the formula:

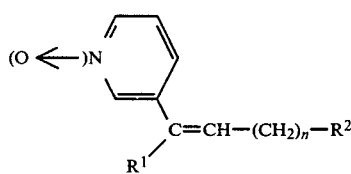

(I)

wherein R$^1$ is an aromatic or heterocyclic group, which may optionally be substituted, R$^2$ is a methyl group, a hydroxymethyl group, a nitroxymethyl group, a formyl group, a nitrogen-containing five-membered ring-methyl group, an acetal-methyl group, a trialkylsilyloxymethyl group, an alkyl- or aryl-sulfonyloxymethyl group, an alkyl- or aryl-sulfonylaminocarbonyloxymethyl group, an acyloxymethyl group, an alkoxycarbonyloxymethyl group, a halogenomethyl group, an alkoxymethyl group, an aryloxymethyl group, a cyano group, a carbamoyl group which may optionally be substituted, a carbamoyloxymethyl group which may optionally be substituted, a thiocarbamoyloxymethyl group which may optionally be substituted, and an alkoxycarbonyl group, n is an integer of 1 to 20 and

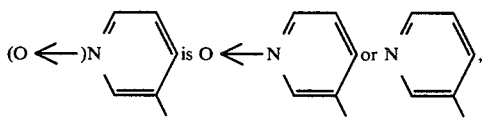

provided that n is an integer of 9 to 20 when

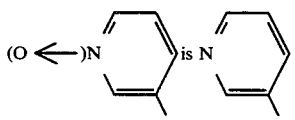

and, at the same time, R$^2$ is a carboxyl group or an alkoxycarbonyl group, or a pharmacologically acceptable salt thereof;

(2) A method of producing a compound of the formula:

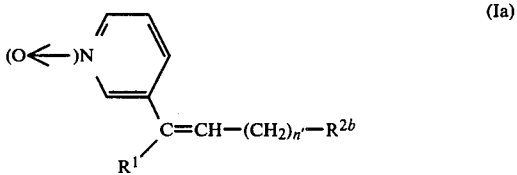

(Ia)

wherein R$^1$ and

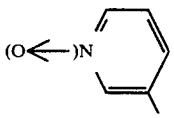

are as defined above and R$^{2b}$ is a methyl group, a hydroxymethyl group, a nitroxymethyl group, a nitrogen-containing five-membered ring-methyl group, an acetal-methyl group, a trialkylsilyloxymethyl group, a halogenomethyl group, an alkoxymethyl group, an aryloxymethyl group, a cyano group, a carbamoyl group which may optionally be substituted, a carboxyl group or an alkoxycarbonyl group, and n' is an integer of 1 to 20, provided that n' is an integer of 9 to 20 when

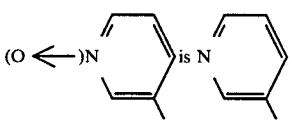

and, at the same time, R$^{2b}$ is a carboxyl group or an alkoxy carbonyl group, which comprises reacting a compound of the formula:

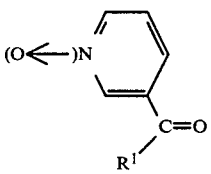

(II)

wherein each symbol is as defined above, with a compound of the formula:

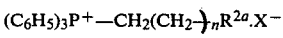

(C$_6$H$_5$)$_3$P$^+$—CH$_2$(CH$_2$)$_n$R$^{2a}$.X$^-$     (III)

wherein R$^{2a}$ is a lower alkyl group, a hydroxymethyl group, a nitroxymethyl group, a nitrogen-containing five-membered ring-methyl group, an acetal-methyl group, a trialkylsilyloxymethyl group, an alkyl- or aryl-sulfonyloxymethyl group, an alkyl- or arylsulfonylaminocarbonyloxymethyl group, an acyloxymethyl group, an alkoxycarbonyloxymethyl group, a halogenomethyl group, an alkoxymethyl group, an aryloxymethyl group, a cyano group, a carbamoyl group which may optionally be substituted, a carbamoyloxymethyl group which may optionally be substituted, a thiocarbamoyloxymethyl group which may optionally be substituted, a carboxyl groups or an alkoxycarbonyl group, X$^-$ is a halide ion and n″ is an integer of 1 to 20, provided that n is an integer of 9 to 20 when R$^{2a}$ is a carboxyl group or an alkoxycarbonyl group and, at the same time,

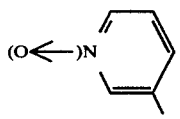

in the formula of the partner compound to be reacted with is

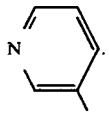

(3) A method of producing a compound of the formula:

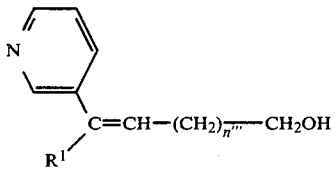
(Ic)

wherein $R^1$ is as defined above and $n'''$ is an integer of 1 to 20, which comprises reducing a compound of the formula:

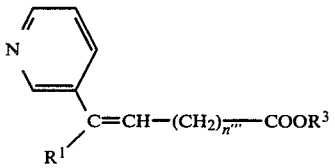
(Ib)

wherein $R^1$ and n are as defined above and $R^3$ is a hydrogen atom, a methyl group, a lower alkoxycarbonyl group or an N-succinimido group;

(4) A method of producing substituted vinyl derivatives of the general formula:

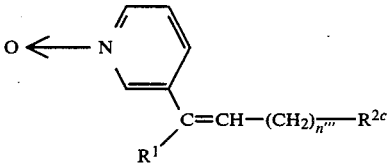
(Ie)

wherein $R^1$ and $n'''$ are as defined above and $R^{2c}$ is a methyl group, a hydroxymethyl group, a nitroxymethyl group, a formyl group, a nitrogen-containing five-membered ring-methyl group, an acetal-methyl group, a trialkylsilyloxymethyl group, an alkyl- or arylsulfonyloxymethyl group, an alkyl- or arylsulfonylaminocarbonyloxymethyl group, an acyloxymethyl group, an alkoxycarbonyloxymethyl group, a halogenomethyl group, an alkoxymethyl group, an aryloxymethyl group, a cyano group, a carbamoyl group which may optionally be substituted, a carbamoyloxymethyl group which may optionally be substituted, a thiocarbamoyloxymethyl group which may optionally be substituted, a carboxyl group or an alkoxycarbonyl group, which comprises oxidizing a compound of the general formula:

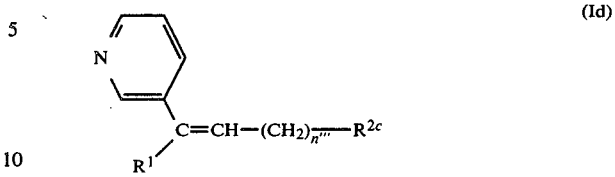
(Id)

wherein $R^1$, $R^{2c}$ and $n'''$ are as defined above.

(5) A method for producing a compound of the formula:

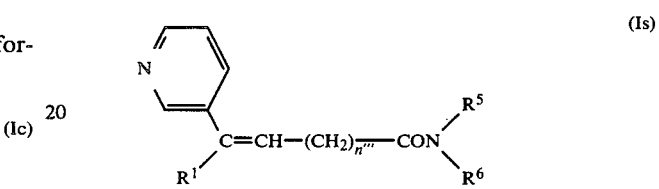
(Is)

wherein $R^1$ and $n'''$ are as defined above, and $R^5$ and $R^6$ are the same or different and each is hydrogen, an alkyl group having 1 to 6 carbon atoms or aryl group having 6 to 8 carbon atoms, which comprises reacting a compound of the formula:

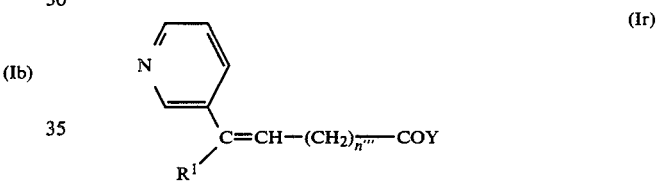
(Ir)

wherein Y is a chlorine atom or a lower alkoxy and $R^1$ and $n'''$ are as defined above, with a compound of the formula:

(V)

wherein $R^5$ and $R^6$ are as defined above.

(6) A pharmaceutical composition containing, as an active ingredient, a substituted vinyl derivative of the general formula (I) or a pharmacologically acceptable salt thereof.

Referring to the above general formulas, the aromatic group represented by $R^1$ includes, among others, aryl groups such as phenyl and naphthyl($\alpha$-naphthyl, $\beta$-naphthyl) and the heterocyclic group includes thienyl(2-thienyl, 3-thienyl), furyl(2-furyl, 3-furyl), pyridyl(2-pyridyl, 3-pyridyl, 4-pyridyl) and benzothienyl(2-benzothienyl, 3-benzothienyl, 4-benzothienyl, 5-benzothienyl, 6-benzothienyl, 7-benzothienyl), among others. These aromatic and heterocyclic groups may have one to three substituents at any position on their ring structure. Said substituent includes lower alkoxy (e.g. such $C_{1-4}$ alkoxy as methoxy, ethoxy, n-propoxy, i-propoxy, n-butoxy, i-butoxy or t-butoxy), lower alkyl (e.g. such $C_{1-5}$ alkyl as methyl, ethyl, n-propyl, i-propyl, n-butyl, i-butyl, t-butyl, n-pentyl or i-pentyl), trifluoromethyl, lower alkenyl (e.g. such $C_{2-5}$ alkenyl as vinyl, allyl or pentenyl), halogen (fluorine, chlorine, bromine, iodine) and methylenedioxy, for instance. The group represented by $R^2$ includes a carboxyl group, a methyl group, a hydroxymethyl group, a nitroxymethyl group, a formyl group, a nitrogen-containing five-membered ring-methyl group, an acetal-methyl group, a trialkylsilyloxymethyl group, an alkyl- or aryl-sulfonyloxymethyl group, an alkyl- or aryl-sulfonylaminocarbonyloxymethyl group, an acyloxymethyl group, an alkoxycarbonyloxymethyl group, a halogenomethyl group, an alkoxymethyl group, an aryloxymethyl group, a cyano group, a carbamoyl group which may optionally be substituted, a carbamoyloxymethyl group which may optionally be substituted, a thiocarbamoyloxymethyl group which may optionally be substituted, and an alkoxycarbonyl group. Said nitrogen-containing five-membered ring-methyl group includes those comprising a methyl group and a five-membered ring group containing 2–4 nitrogen atoms, which is the substituent on said methyl group, such as imidazolylmethyl groups (1-imidazolylmethyl, 2-imidazolylmethyl), triazolylmethyl groups (1-triazolylmethyl, 3-triazolylmethyl, 5-triazolylmethyl) and tetrazolylmethyl groups (1-tetrazolylmethyl, 5-tetrazolylmethyl). Said acetalmethyl group is one having 2 to 7 carbon atoms and is, for example, 2-tetrahydropyranyloxymethyl or 2-tetrahydrofuryloxymethyl; said trialkylsilyloxymethyl group is one having 4 to 10 carbon atoms and is, for example, dimethyl-tert-butylsilyloxymethyl; said alkyl- or aryl-sulfonyloxymethyl is $C_{1-3}$ alkyl- or $C_{6-7}$ aryl- one and is, for example, methanesulfonyloxymethyl or p-toluenesulfonyloxymethyl; said alkyl- or arylsulfonylaminocarbonyloxymethyl group is $C_{1-3}$ alkyl- or $C_{6-7}$ aryl- one and is, for example, methanesulfonylaminocarbonyloxymethyl or p-toluenesulfonylaminocarbonyloxymethyl; said acyloxymethyl group may be a group of the formula $R^4COOCH_2$— in which $R^4$ is hydrogen, $C_{1-6}$ alkyl (e.g. methyl, ethyl, n-propyl, i-propyl, n-butyl, i-butyl, n-pentyl, i-pentyl, n-hexyl) or pyridyl (2-pyridyl, 3-pyridyl, 4-pyridyl); said alkoxycarbonyloxymethyl group includes, among others, those containing 3–8 carbon atoms such as methoxycarbonyloxymethyl, ethoxycarbonyloxymethyl, n-propoxycarbonyloxymethyl, i-propoxycarbonyloxymethyl, n-butoxycarbonyloxymethyl, i-butoxycarbonyloxymethyl, n-pentyloxycarbonyloxymethyl and n-hexyloxycarbonyloxymethyl; the halogenomethyl group includes, fluorometyl, chloromethyl, bromomethyl, and iodomethyl; said alkoxymethyl group includes, among others, lower ones containing 2–5 carbon atoms, such methoxymethyl, ethoxymethyl, n-propoxymethyl, i-propoxymethyl, n-butoxymethyl and i-butoxymethyl; said aryloxymethyl group includes, among others, those containing 7–9 carbon atoms, such as phenyloxymethyl, 2-methylphenyloxymethyl, 3-methylphenyloxymethyl, 4-methylphenyloxymethyl, 2,4-dimethylphenyloxymethyl and 3,4-dimethylphenyloxymethyl; said carbamoyl group, which may optionally be substituted, may be of the formula:

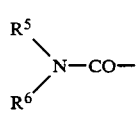

wherein $R^5$ and $R^6$ are the same or different and each is hydrogen, $C_{1-6}$ alkyl (e.g. methyl, ethyl, n-propyl, i-propyl, n-butyl, i-butyl, t-butyl, n-pentyl, i-pentyl, n-hexyl, i-hexyl) or $C_{6-8}$ aryl (e.g. phenyl, 2-methylphenyl, 3-methylphenyl, 4-methylphenyl, 2,4-dimethylphenyl, 3,4-dimethylphenyl); said carbamoyloxymethyl group, which may optionally be substituted, may be of the formula

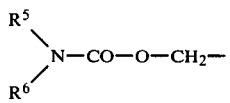

wherein $R^5$ and $R^6$ are as defined above; and said thiocarbamoyloxy group which may optionally be substituted may be of the formula:

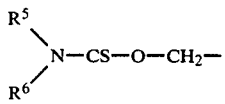

wherein $R^5$ and $R^6$ are as defined above. Said alkoxycarbonyl group includes those containing 2–5 carbon atoms, such as methoxycarbonyl, ethoxycarbonyl, n-propoxycarbonyl, i-propoxycarbonyl, n-butoxycarbonyl, i-butoxycarbonyl and t-butoxycarbonyl. The substituent groups represented by $R^{2a}$, $R^{2b}$ and $R^{2c}$ each includes, among others those specific groups given as example of the corresponding group represented by $R^2$. The lower alkyl group represented by $R^3$ includes those containing 1–4 carbon atoms, such as methyl, ethyl, n-propyl, i-propyl, n-butyl, i-butyl and t-butyl, and the lower alkoxycarbonyl group includes those containing 2–5 carbon atoms, such as methoxycarbonyl, ethoxycarbonyl, n-propoxycarbonyl, i-propoxycarbonyl, n-butoxycarbonyl, i-butoxycarbonyl and t-butoxycarbonyl. The halide ion represented by X is, for instance, a chlorine, bromide or iodide ion.

The pharmacologically acceptable salt of the compound of general formula (I) is an addition salt with an organic or inorganic salt, for example, hydrochloric acid, hydrobromic acid, phosphoric acid, sulfuric acid, citric acid, succinic acid, maleic acid, fumaric acid, oxalic acid, methanesulfonic acid or benzenesulfonic acid. In cases where $R^2$ in compounds (I) is a carboxyl group, it may be an alkali metal salt (e.g. sodium salt, potassium salt) or an alkaline earth metal salt (e.g. calcium salt).

For each compound of general formula (II), there are two geometric isomers representable by the general formulas:

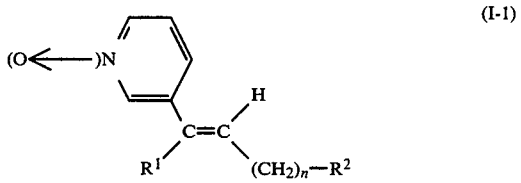

(I-1)

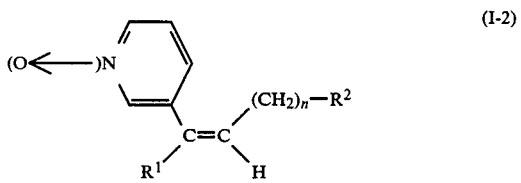

(I-2)

wherein each symbol is as defined above. Generally, those compounds represented by general formula (I-1) are pharmacologically superior to those represented by general formula (I-2) in that the former are stronger in thomboxane synthetase inhibiting activity.

Hereinafter, the compounds represented by general formula (I-1) in which the substituent pyridine ring on one carbon atom involved in the vinyl double bond and the hydrogen atom on the other carbon atom involved in said double bond are oriented in the same direction are referred to as E isomers while those represented by general formula (I-2) in which the pyridine ring on one carbon atom involved in the double bond and the hydrogen atom on the other carbon atom involved in said bond are oriented in the opposite directions are referred to as Z isomers.

The E isomers represented by the general formula:

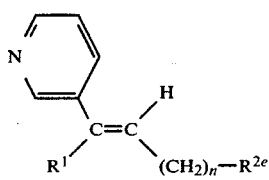

(Iv)

wherein $R^1$ and n are as defined above and $R^{2e}$ is a methyl group or a carboxyl group, can be produced by heating a compound of the general formula:

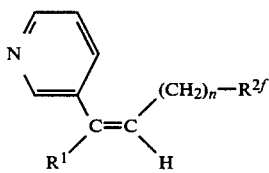

(Iw)

wherein $R^1$ and n are as defined above and $R^{2f}$ is a methyl group, a cyano group, a carbamoyl group which may optionally be substituted, a carboxyl group or an alkoxycarbonyl group, in the presence of an mineral acid.

Each of the substituent groups represented by the above $R^{2e}$ and $R^{2f}$ includes, among others, those specific groups given as examples of the corresponding substituent group represented by $R^2$.

The above acid treatment is generally conducted in water or an aqueous organic solvent. Any aqueous organic solvent which is not decomposed by the mineral acid may be used. Examples are mixed solvents composed of acetic acid, formic acid or the like and water. The mineral acid is, for example, hydrochloric acid, sulfuric acid, phosphoric acid, hydrobromic acid, perchloric acid or methanesulfonic acid. Preferred are hydrochloric acid, hydrobromic acid and phosphoric acid. These acid catalysts are used generally in an amount of about 6-15 moles per mole of the starting compound (Iw). The reaction temperature is generally within the range of about 50°-140° C., preferably 100°-130° C. At lower temperatures, the rate of isomerization reaction is slow. The reaction time, which depends on the kind and amount of acid catalyst and the heating temperature, is generally selected within the range such that the acid isomerization reaches equilibrium in 10-40 hours.

This reaction produces an equilibrium state between the E isomer (Iv) and the Z isomer (Iw). The E or Z isomer alone or a mixture of both the isomers in any proportion, when subjected to the isomerization reaction, gives a mixture composed of the E isomer (Iv) (about 60-70%) and the Z isomer (Iw) (about 30-40%). Since the E isomer is in general superior pharmacologically to the Z isomer, as mentioned hereinbefore, it is desirable to apply this reaction to a mixture containing the Z isomer in a proportion of 40% or more.

When a compound of general formula (Iw) in which $R^2$ is a cyano group, carbamoyl group which may optionally be substituted or an alkoxycarbonyl group is used as the starting material in this reaction, hydrolysis proceeds simultaneously to give the corresponding carboxyl compound.

The intended compound (Iv) (E isomer) produced by this reaction can be extracted with an organic solvent such as ethyl acetate, chloroform or dichloromethane from the reaction mixture following adjustment of the pH of said mixture to 5.0-6.0 with aqueous ammonia, sodium hydroxide or potassium hydroxide, for instance. Thereafter, the compound (Iv) can be isolated and purified by the per se known techniques, such as recrystallization or chromatography. The chemical isolation yield of E isomer (Iv) can be increased by subjecting the Z isomer-rich mixture obtained after separation of E isomer (Iv) or removal thereof by repeated fractional recrystallization to this isomerization reaction.

The substituted vinyl derivatives represented by the above general formula (I) and phamacologically acceptable salts thereof [hereinafter sometimes collectively referred to as "compounds (I)"] are capable of inhibiting thromboxane synthetase isolated from the platelet microsomes of humans, horses or the like, and exhibit strong and lasting, thromboxane $A_2$ ($TXA_2$) synthetase inhibiting activity in mammals including humans.

Furthermore, the compounds (I) according to the invention are capable of increasing the efficiency of production of prostaglandin $I_2$ ($PGI_2$) which exhibits arterial smooth muscle dilating action, platelet aggregation inhibiting activity or aggregated platelet dissociating activity. The compounds (I) of the invention inhibit, in very low doses (1-10 mg/kg), thromboxane $A_2$ synthetase, i.e. the enzyme required for the conversion of prostaglandin $G_2$ ($PGG_2$) or prostaglandin $H_2$ ($PGH_2$), which is an important precursor in synthesis of thromboxane $A_2$, prostaglandin $I_2$ and other prostaglandins, to thromboxane $A_2$, whereas they hardly inhibit those enzymes which are required for the conversion to physiologically very useful prostaglandin $I_2$ ($PGI_2$) and other prostaglandins, for example $PGI_2$ synthetase and various prostaglandin synthetases, but rather increase the efficiency of utilization of $PGH_2$ or $PGG_2$ in vivo. Thus, for instance, they increase the production of $PGD_2$ in platelets, and of $PGI_2$ in the presence of vascular endothelial cells. In that respect, those compounds in which $R^2$ in general formula (I) is a carboxyl group have very strong activity. Those compounds in which $R^2$ in general formula (I) is other than a carboxyl group themselves have the activity mentioned above but are presumably converted in vivo to the compounds in which $R^2$ is a carboxyl group, so that in in vivo experiments, they are almost comparable to the above activity to those compounds in which $R^2$ is a carboxyl group.

In this way, the compounds (I) of this invention do not inhibit prostaglandin $I_2$ ($PGI_2$) synthetase, prostaglandin synthetase (cyclooxygenase) or synthetases for various prostaglandins, but strongly and persistently inhibit thromboxane $A_2$ ($TXA_2$) synthetase in a selective manner.

Furthermore, those compounds in which $R^2$ in general formula (I) is $ONO_2$ have smooth muscle relaxing activity in addition to the above activity.

Moreover, the compounds of the invention are very low in toxicity in rats, dogs and so forth and characterized by broad margin between the toxic dose and the therapeutically effective dose. For example, no rat was dead for 14 days when (E)-7-phenyl-7-(3-pyridyl)-6-hepten-1-ol was orally administered in an amount of 1000 mg/kg/day to five rats. Furthermore, the compounds (I) of the invention produced long-lasting pharmacological effects in vivo, so that their $TXA_2$ synthetase inhibiting activity is expected to be retained stably for a prolonged period of time. Accordingly, the compounds provided by the invention are used in low doses in mammals, including humans, for the prevention or treatment of thrombosis due to $TXA_2$-induced platelet aggregation, ischemic diseases due to vasospasm in heart, brain, periphery and circulatory system (e.g. myocardial infarction, stroke, renal infarction, pulmonary infarction, infarction at some other site, digestive tract ulcer) and diseases due to imbalance of the ratio of $TXA_2/PGI_2$, with low incidence of adverse effects resulting from long-term continuous use thereof. They are administered orally in the form of tablets, capsules, powders or granules, for instance, or parenterally in the form of injections or pellets. Generally, they are used in a daily oral dose of 20-200 mg per adult human or a daily parenteral dose of 10-100 mg per adult human, respectively in 1-3 divided doses.

The substituted vinyl derivative of the general formula (I) can be produced by any of the following processes.

[Production Process 1]

A compound of the general formula (Ia) can be produced by reacting a compound of general formula (II) with a compound of general formula (III).

This reaction is generally carried out in the presence of a base in an organic solvent. As examples of said base may be mentioned n-butyllithium, lithium diisopropylamide, sodium hydride, potassium hydride, potassium tert-butoxide and sodium amide. Preferred are lithium diisopropylamide, sodium hydride and sodium amide. The solvent may for example be ether, tetrahydrofuran, dimethyl sulfoxide or dimethylformamide, or a mixture of two or more such solvents. This reaction is preferably conducted in a dry inert gas (for example, nitrogen gas, argon gas, and helium gas). The reaction temperature is generally $-70°$ C. to $+30°$ C., although it depends on the kinds of the solvent and base used. The progress and rate of this reaction can be ascertained by the disappearance of the characteristic color of phosphorane. Generally the reaction goes to completion in about 1 to 6 hours.

A compound of general formula (III) in which $R^{2a}$ is alkylsulfonyloxymethyl, arylsulfonyloxymethyl, alkylsulfonylaminocarbonyloxymethyl, arylsulfonylaminocarbonyloxymethyl, acyloxymethyl, alkoxycarbonyloxymethyl, substituted or unsubstituted carbamoyloxymethyl or substituted or unsubstituted thiocarbamoyloxymethyl, when used as the starting compound (III) in the above reaction, may sometimes give the compound (Ia) in which $R^{2b}$ is hydroxymethyl.

[Production Process 2]

A substituted vinyl derivative of general formula (Ic) can be produced by reducing a compound of general formula (Ib).

Referring to the general formula (Ib), the carboxylic acid or an ester thereof wherein $R^3$ is a hydrogen atom or a lower alkyl group can generally be converted to the corresponding alcohol (Ic) by reacting it with lithium aluminum hydride in a solvent such as diethyl ether, tetrahydrofuran and 1,2-dimethoxyethane. This reduction reaction proceeds readily when $R^3$ is a lower alkyl group. The reaction temperature is $-10°$ C. to $+70°$ C., and at room temperature the reaction goes to completion in 1 to 10 hours. The reducing agent is used in an amount of 1-2 moles per mole of compound (Ib). Following completion of the reaction, the excess reducing agent is decomposed and the contemplated compound is extracted by the per se conventional procedure.

The compound of general formula (Ib) wherein $R^3$ is a lower alkoxycarbonyl group or a succinimido group can be converted to the corresponding alcohol (Ic) by reducing it with sodium borohydride, potassium borohydride or the like in methanol, ethanol, diethylether, tetrahydrofuran or 1,2-dimethoxyethane or a mixture thereof with water.

[Production Process 3]

A substituted vinyl derivative of general formula (Ie) can be produced by oxidizing a compound of general formula (Id).

In the above reaction, a compound of general formula (Id) is treated with an oxidizing agent in a suitable solvent. The preferable oxidizing agent to be used is a peroxide such as hydrogen peroxide, peracetic acid, perbenzoic acid or m-chloroperbenzoic acid and the preferable solvent to be used is water or an organic solvent such as chloroform, methylene chloride, acetic acid or ethyl acetate. The reaction temperature is generally $-30°$ C. to $+50°$ C., preferably $-10°$ C. to $+30°$ C.

[Production Process 4]

A compound of general formula:

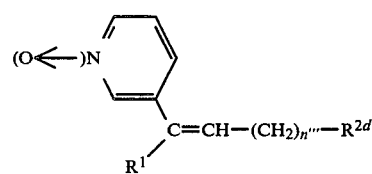
(Ig)

wherein $R^1$, $n'''$ and

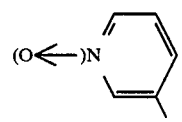

are as defined hereinbefore; $R^{2d}$ is acyloxymethyl, substituted or unsubstituted carbamoyloxymethyl, substituted or unsubstituted thiocarbamoyloxymethyl, alkyl- or arylsulfonylaminocarbonyloxymethyl, or alkoxycarbonyloxymethyl, can be produced by acylation, carbamoylation, thiocarbamoylation, alkyl- or arylsulfonylaminocarbonylation, or alkoxycarbonylation of a compound of general formula

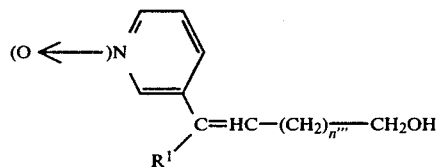
(If)

wherein each symbol is as defined hereinbefore.

Referring to the general formula (Ig), acyloxymethyl, substituted or unsubstituted carbamoyloxymethyl, substituted or unsubstituted thiocarbomoyloxymethyl, or alkyl- or arylsulfonylaminocarbonyloxymethyl represented by $R^{2d}$ are respectively the same as those represented by $R^2$.

The acylation or alkoxycarbonyloxylation reaction is conducted by reacting the corresponding acid chloride, acid anhydride, or chlorocarbonic acid ester with a compound of general formula (Ic) in the presence of a base (e.g. triethylamine, pyridine). This reaction is carried out in dimethylformamide, pyridine or chloroform, generally at a temperature of $-10°$ C. to $+30°$ C. Said acid anhydride includes acetic anhydride, propionic anhydride and benzoic anhydride; said acid chloride includes acetyl chloride, butyryl chloride, isobutyryl chloride, nicotinoyl chloride and benzoyl chloride; and said chlorocarbonic acid ester includes methyl chlorocarbonate, ethyl chlorocarbonate, benzyl chlorocarbonate and t-butyl chlorocarbonate.

The (substituted)-carbamoylation, (substituted)-thiocarbamoylation and alkyl- or arylsulfonylaminocarbonylation and the like reaction can be conducted using a cyanic acid salt or a thiocyanic acid salt in the presence of an organic or inorganic acid (e.g. trifluoroacetic acid, methanesulfonic acid, hydrochloric acid), using an alkyl- or arylcyanic acid, an alkyl- or arylthiocyanic acid in the presence of triethylamine or pyridine, or using an alkyl- or arylsulfonylcyanic acid.

The cyanate or thiocyanate is, for example, sodium cyanate, potassium cyanate, sodium thiocyanate or potassium thiocyanate. The alkyl or aryl moiety of the alkyl- or arylcyanate, alkyl- or aryl-thio- or -sulfonyl-cyanate is, for example, methyl, ethyl, isopropyl, propyl, butyl, isobutyl, phenyl, or 3-pyridyl.

The reaction is conducted at $0°–50°$ C. for 1–10 hours, in the presence or absence of an anhydrous solvent (e.g. chloroform, methylene chloride).

[Production Process 5]

A compound of the general formula:

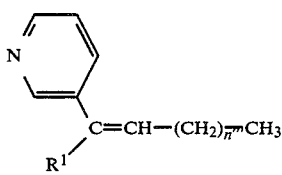
(Ii)

wherein $R^1$, and $n'''$ are as defined hereinbefore, can be produced by reducing a compound of general formula:

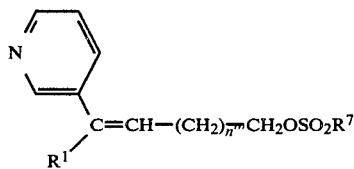
(Ih)

wherein $R^1$ and $n'''$ are as defined hereinbefore and $R^7$ is alkyl or aryl.

Referring to the general formula (Ih), the alkyl or aryl represented by $R^7$ is, for example, methyl or p-tolyl and $-CH_2OSO_2R^7$ is the same as the alkyl- or arylsulfonyloxymethyl represented by $R^2$.

Generally, this reduction reaction is conducted using a reducing agent such as lithium aluminum hydride or sodium cyanoborohydride in an atmosphere of argon, helium and/or nitrogen in hexamethylphosphoramide or in an ether solvent such as dimethyl ether, tetrahydrofuran or 1,2-dimethoxyethane. The reduced agent is preferably used in an amount of 0.5–2 moles per mole of compound (Ih) and the reaction is carried out generally at a temperature of $10°–80°$ C.

[Production Process 6]

A halogen compound of the general formula:

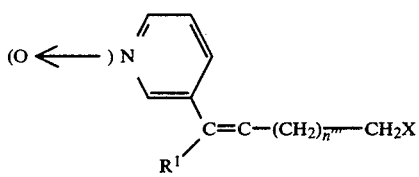
(Ik)

wherein $R^1$, $n'''$ and

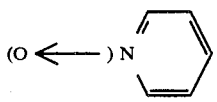

are as defined hereinbefore and X is a halogen atom, can be obtained by reacting a compound of the general formula

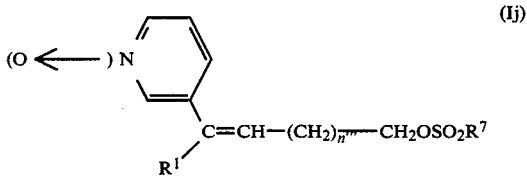
(Ij)

wherein each symbol is as defined hereinbefore, with a halide.

Referring to the general formula (Ik), the halogen atom represented by X is fluorine, chlorine, bromine or iodine and $-CH_2X$ is the same as the halogenomethyl represented by $R^2$.

The reaction is conducted in the manner of exchange reaction with sodium bromide, potassium bromide sodium iodide, potassium iodide or triethylamine hydrochloric acid salt, for instance, in a solvent such as methylene chloride, chloroform, acetone, methanol, aqueous acetone or aqueous methanol. Generally, the reaction is conducted at 0°–50° C. and goes to completion in 1–20 hours.

[Production Process 7]

A compound of general formula:

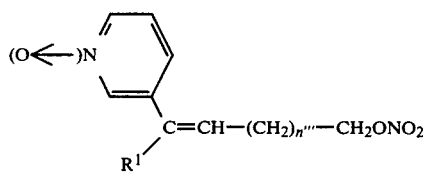
(II)

wherein $R^1$, $n'''$ and

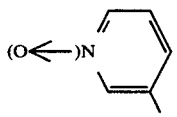

are as defined hereinbefore, can be produced by reacting a compound of general formula (Ij) or (Ik) with silver nitrate.

This reaction is generally conducted in a solvent such as acetonitrile, dioxane, 1,2-dimethoxyethane or acetone. The silver nitrate is preferably used in an amount of 1–1.2 moles per mole of compound (Ij) or (Ik). The reaction is generally conducted at room temperature for 2–5 hours.

[Production Process 8]

A compound of general formula:

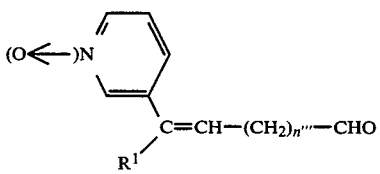
(In)

wherein $R^1$, $n'''$ and

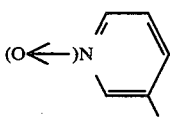

are as defined hereinbefore can be produced by oxidizing a compound of general formula:

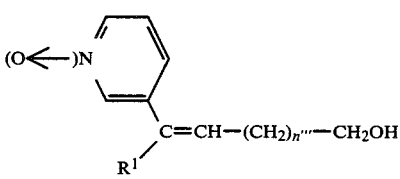
(Im)

wherein each symbol is as defined hereinbefore.

Generally, this reaction can readily be effected by known techniques for converting alcohols to aldehydes. For example, the compound (Im) is oxidized with a chromic acid-pyridine complex or a dimethyl sulfoxide-oxalyl chloride-triethylamine mixture.

[Production Process 9]

A compound of general formula:

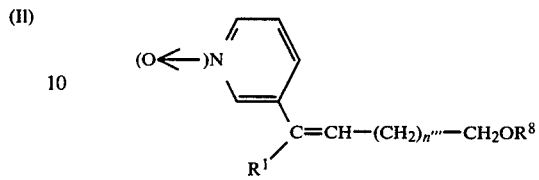
(Io)

wherein $R^1$, $n'''$ and

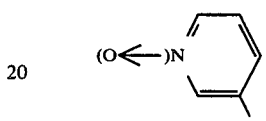

are as defined hereinbefore and $R^8$ is alkyl or aryl, can be produced by reacting a compound of general formula (Ij) or (Ik) with an alkoxide or aryloxide of an alkali metal.

Referring to general formula (Io), the alkyl and aryl represented by $R^8$ is, for example, methyl or p-tolyl and $-CH_2OR^8$ is the same as the alkoxymethyl or aryloxymethyl represented by $R^2$.

The above reaction is carried out in an alcohol or phenol corresponding to the alkoxy or aryloxy group using a sodium or potassium alkoxide or phenoxide corresponding to said group. Said alkoxide is, for example, methoxide, ethoxide or propoxide. Said alcohol is, for example, methanol, ethanol or propanol.

[Production Process 10]

A compound of general formula:

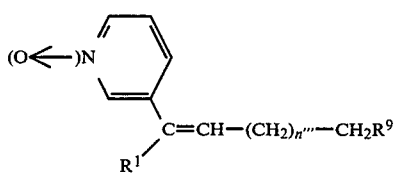
(Ip)

wherein $R^1$, $n'''$ and

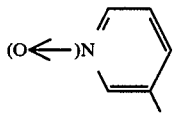

are as defined hereinbefore and $R^9$ is an acetal group, can be produced by reacting a compound of general formula (Im) with dihydropyran or dihydrofuran in the presence of an acid catalyst.

Referring to general formula (Ip), the acetal represented by $R^9$ is, for example, 2-tetrahydropyranyloxy or 2-tetrahydrofuryloxy and $-CH_2R^9$ is the same as the acetal-methyl represented by $R^2$.

The above reaction is carried out generally in the presence of an acid catalyst. The acid catalyst is, for example, p-toluenesulfonic acid or camphorsulfonic acid. As the solvent, dry chloroform or methylene chloride is frequently used. Generally, the reaction is conducted at 0°-30° C. and goes to completion in 1-3 hours.

[Production Process 11]

A compound of general formula:

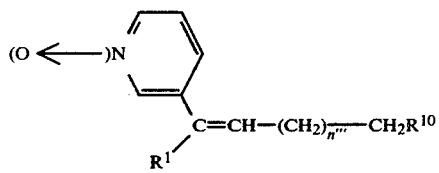

wherein $R^1$ and $n'''$ are as defined hereinbefore and $R^{10}$ is a nitrogen-containing 5-membered ring, can be produced by reacting a compound of general formula (Ik) with a compound of general formula:

wherein $R^{10}$ is as defined hereinbefore.

Referring to general formula (Iq), the nitrogen-containing 5-membered ring represented by $R^{10}$ is the same as the corresponding moiety of the nitrogen-containing 5-membered ring-methyl $CH_2R^{10}$ represented by $R^2$.

The above reaction is carried out generally in the presence of a base such as sodium hydride or potassium t-butoxide. As the solvent, dimethylformamide, dimethyl sulfoxide, 1,2-dimethoxyethane or t-butanol is used and the reaction is conducted generally at 0°-50° C.

[Production Process 12]

A compound of general formula:

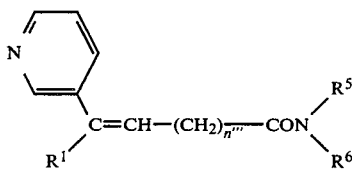

wherein each symbol is as defined hereinbefore, can be produced by reacting a compound of general formula:

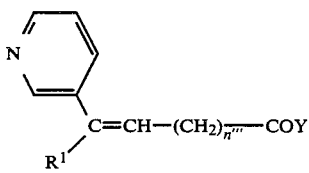

wherein Y is a chlorine atom or lower alkoxy and $R^1$ and n are as defined hereinbefore, with a compound of the general formula:

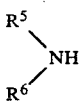

wherein $R^5$ and $R^6$ are as defined hereinbefore.

Generally, the above amidation reaction can be conducted by an appropriate known method. Thus, for example, when Y in general formula (Ir) is an alkoxy, the compound (Ir) can be reacted with the amine compound in a solvent, such as methanol, ethanol, dioxane or toluene, or without using any solvent, in the temperature range of 0°-100° C. When Y in general formula (Ir) is a chlorine atom, the reaction can be carried out in a solvent, such as methylene chloride, chloroform, acetone or an aqueous solvent, in the presence of pyridine, triethylamine, sodium carbonate, potassium carbonate or the like.

[Production Process 13]

A compound of general formula:

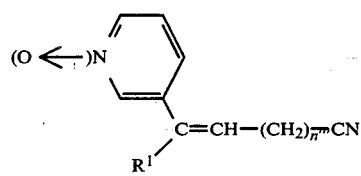

wherein each symbol is as defined hereinbefore, can be produced by reacting a compound of general formula (Ij) or (Ik) with sodium cyanide or potassium cyanide.

This reaction can generally be carried out by an appropriate known method of cyanation. For instance, dimethyl sulfoxide or dimethylformamide may be used as the solvent. When conducted at 0°-30° C., the reaction will be complete in 5-20 hours.

[Production Process 14]

A compound of general formula:

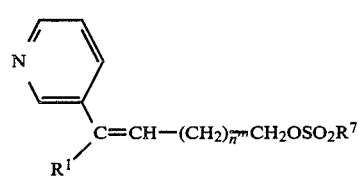

wherein each symbol is as defined hereinbefore, can be produced by reacting a compound of general formula (Ic) with a compound of general formula:

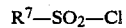

wherein $R^7$ is as defined hereinbefore.

The above reaction can be conducted in the presence of pyridine or triethylamine in a solvent such as dimethylformamide, methylene chloride or chloroform at a temperature in the range of 0°-30° C.

[Production Process 15]

A compound of general formula:

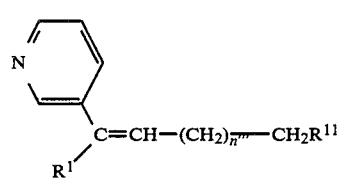

wherein $R^1$ and n are as defined hereinbefore and $R^{11}$ is trialkylsilyloxy, can be produced by reacting a compound of general formula (Ic) with trialkylsilyl chloride in the presence of pyridine or triethylamine.

Referring to the above general formula (Iu), the trialkylsilyloxy represented by $R^{11}$ is the same as the corresponding moiety of the trialkylsilyloxymethyl —$CH_2R^{11}$ represented by $R^2$.

The above reaction can be carried out generally in methylene chloride or chloroform in the temperature range of 0°–30° C.

The thus-produced substituted vinyl derivative (I) can be separated and purified by the conventional procedure, for instance, extraction, concentration, crystallization, liquid chromatography or the like. Compound (I) belongs to the class of tri-substituted olefins. In some instances, the compound (I) involves two geometric isomers. Separation of the isomers can be performed, as necessary, by fractional crystallization or chromatography, for instance.

The compound of the above general formula (II) can be produced, as schematically illustrated below, by preparing a compound (VII) by reaction of organolithium compound and aldehyde and then reacting the compound (VII) with manganese dioxide or dimethyl sulfoxide-oxalyl chloride.

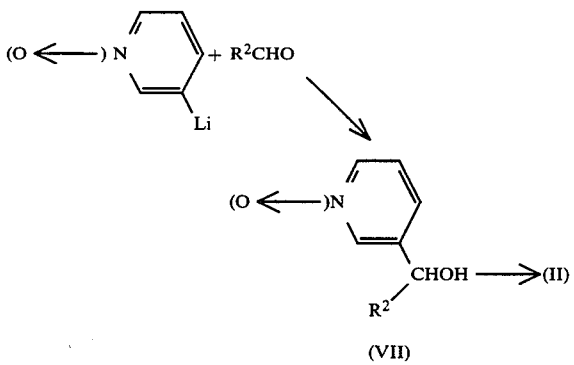

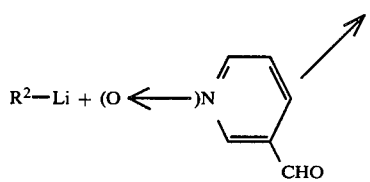

In the above formulas, each symbol is as defined hereinbefore.

The following examples, experimental examples and reference examples are given to illustrate this invention in further detail.

EXAMPLE 1

(Compound Id-1)

In a nitrogen stream, sodium amide (3,12 g, 80 mmoles) was added to dimethyl sulfoxide (35 ml) and the mixture was stirred at room temperature for 10 minutes. While maintaining a temperature not exceeding 40° C., hexyltriphenylphosphonium bromide (33.7 g, 79 mmoles) was added to the above solution and the mixture was stirred for an hour, followed by addition of a dimethyl sulfoxide solution (30 ml) containing 3-benzoylpyridine (14.5 g, 79 mmoles) at room temperature. After completion of the addition, the reaction was allowed to proceed at room temperature for 30 minutes, and then, 2N hydrochloric acid (500 ml) was added and the neutral component was extracted with toluene. The aqueous layer was made alkaline with sodium carbonate and the oily product was extracted twice with ether. These ether layers were combined, washed with water, dried (magnesium sulfate) and concentrated under reduced pressure. The residue was subjected to silica gel column chromatography using isopropyl etherethyl acetate (4:1) as the developing solvent to give 1-phenyl-1-(3-pyridyl)-1-heptene (18.2 g, 92%) as an isomeric mixture (E:Z=1:1).

Compounds Id-1 to Id-7 produced by the above procedure of Example 1 are listed in Table 1.

TABLE 1

| Compound | $R^1$ | $R^{2c}$ | n | Isomer(s) | Prepared by the procedure of Example | Molecular formula (physical properties) | Nuclear magnetic resonance spectrum, δ values, TMS as internal standard |
|---|---|---|---|---|---|---|---|
| Id-1 | phenyl | $CH_3$ | 4 | E + Z | 1 | $C_{18}H_{21}N$ Oil | 8.47(1H,d,2Hz), 8.43(1H,d,2 Hz,4Hz), 7.39(E), 7.23(Z)(6H,m), 6.27(E), 6.18(Z)(1H,t,7Hz), 2.18(2 H,m), 1.65(6H,m), 0.86(3H,t) |
| Id-2 | thienyl | $CH_3$ | 4 | E + Z | 1 | $C_{16}H_{19}NS$ Oil | 8.54(1H,d,2Hz), 8.48(2H,dd,2 Hz,4Hz), 7.56(1H,m), 7.25(1H,m), 7.10(1H,m), 7.03(1H,m), 6.88(1H,m), 6.22(Z), 6.03(E)(1H,m), 2.20(2H,m), 1.65 (6H,m), 0.86(3H,t) |
| Id-3 | thienyl | $CH_3$ | 4 | E + Z | 1 | $C_{16}H_{19}NS$ Oil | 8.48(2H,m), 7.20(4H,m), 6.98 & 6.87(1H,m), 6.21 & 6.06(1H,t,7 Hz), 2.18(2H,m),1.65(8H,m), 0.86(3H,t) |

TABLE 1-continued

| Compound | R¹ | R²ᶜ | n | Isomer(s) | Prepared by the procedure of Example | Molecular formula (physical properties) | Nuclear magnetic resonance spectrum, δ values, TMS as internal standard |
|---|---|---|---|---|---|---|---|
| Id-4 | (4-methylenedioxyphenyl) | $CH_3$ | 4 | Z | 1,14 | $C_{19}H_{21}NO_2$ Oil | 8.45(2H,m), 7.51(1H,m), 7.37(1H, m), 6.68(1H,d,2Hz), 6.68(1H,d,8 Hz), 6.53(1H,dd,2Hz,8Hz), 6.05(1 H,t,7Hz), 5.92(2H,s), 2.08(2H,m), 1.62(6H,m), 0.85(3H,t) |
| Id-5 | (phenyl) | $CH_3$ | 4 | E | 1,14 | $C_{18}H_{21}N$ 49–50° C. | 8.46(1H,d,2Hz), 8.43(1H,dd, 2Hz,4Hz), 7.39(6H,m), 7.80(1H, dt,2Hz,4Hz), 6.27(1H,t,7Hz), 2.17(2H,m), 1.64(6H,m), 0.86(3 H,t) |
| Id-6 | (phenyl) | $CH_3$ | 4 | Z | 1,14 | $C_{18}H_{21}N$ Oil | 8.46(1H,d,2Hz), 8.42(1H,dd, 2Hz,4Hz), 7.23(6H,m), 6.18(1H, t,7Hz), 2.18(2H,m), 1.65(6H, m), 0.86(3H,t) |
| Id-7 | (thienyl) | $CH_3$ | 4 | E | 1,14 | $C_{16}H_{19}NS$ Oil | 8.53(2H,m), 7.62(1H,m), 7.20(1 H,m), 7.15(1H,m), 6.83(1H,m), 6.48(1H,m), 6.20(1H,t,7Hz), 2.20(2H,m), 1.65(6H,m), 0.86 (3H,t) |

EXAMPLE 2

(Compounds Id-8 and Id-9)

Sodium hydride (60% dispersion in oil, 2.7 g, 68 mmoles) was washed with hexane and, after removal of the hexane under reduced pressure, dimethyl sulfoxide (40 ml) was added and the mixture was stirred with heating at 85° C. for an hour. After cooling, a dimethyl sulfoxide solution (20 ml) containing 10-carboxydecyl-triphenylphosphonium bromide (18.0 g, 34 mmoles) was added dropwise to the mixture. After 10 minutes, a solution of 3-benzoylpyridine (6.2 g, 33.8 mmoles) in dimethyl sulfoxide (10 ml) was added. The reaction was allowed to proceed for an hour and, following addition of water (200 ml), the reaction product was washed with toluene. The aqueous layer was acidified with 2N hydrochloric acid to pH 5.2, and the product was extracted with ethyl acetate. The organic layer was washed with water, dried and distilled under reduced pressure to remove the solvent. The residue was then subjected to silica gel column chromatography using ethyl acetate as the developing solvent to give (Z)-12-phenyl-12-(3-pyridyl)-11-dodecenoic acid (Compound Id-8, 3.2 g), after fractional recrystallization from isopropylether.

The crystallization mother liquor was dissolved in ethanol (20 ml) and thionyl chloride (3 ml) was added to the solution. The mixture was allowed to stand at room temperature for 3 hours and concentrated under reduced pressure, and 5% aqueous sodium carbonate (50 ml) was added. After extraction of the product with methylene chloride, the organic layer was washed with water, dried and concentrated. The residue was subjected to silica gel column chromatography using isopropyl ether as the developing solvent and the thus-obtained ethyl ester was hydrolyzed to give (E)-12-phenyl-12-(3-pyridyl)-11-dodecenoic acid (Compound Id-9, 2.3 g).

Compounds Id-10 to Id-13 produced by the above procedure of this example are listed in Table 2.

TABLE 2

| Compound | R¹ | R²ᶜ | n | Isomer(s) | Prepared by the procedure of Example | Molecular formula (physical properties) | Nuclear magnetic resonance spectrum, δ values, TMS as internal standard |
|---|---|---|---|---|---|---|---|
| Id-8 | (phenyl) | COOH | 9 | Z | 2 | $C_{23}H_{29}NO_2$ 94–95° C. | 9.52 (COOH), 8.54 (1H, dd, 2Hz, 4 Hz), 8.46 (1H, d, 2Hz), 7.53 (1H, dt, 7Hz, 2Hz), 7.20 (5H, m), 6.15 (1H, t, 7Hz), 2.32 (2H, m), 2.08 (2H, m), 1.25 (14H, m) |

TABLE 2-continued

| Compound | R¹ | R²ᶜ | n | Isomer(s) | Prepared by the procedure of Example | Molecular formula (physical properties) | Nuclear magnetic resonance spectrum, δ values, TMS as internal standard |
|---|---|---|---|---|---|---|---|
| Id-9 | 3-pyridyl | –CO–OH | 9 | E | 2 | $C_{23}H_{29}NO_2$ Oil | 9.42 (COOH), 8.45 (2H, m), 7.30 (7H, m), 6.12 (1H, t, 7Hz), 2.28 (4H, m), 1.25 (14H, m) |
| Id-10 | 3-pyridyl | –CO–OH | 8 | Z | 2 | $C_{22}H_{27}NO_2$ Oil | 9.38 (COOH), 8.56 (2H, m), 8.47 (1H, d, 2Hz), 7.53 (1H, m), 7.20 (5H, m), 6.15 (1H, t, 7Hz), 2.33 (2H, m), 2.09 (2H, m), 1.25 (12H, m) |
| Id-11 | 3-pyridyl | –CO–OH | 8 | E | 2 | $C_{22}H_{27}NO_2$ Oil | 9.46 (COOH), 8.48 (2H, m), 7.53 (1H, m), 7.20 (5H, m), 6.12 (1H, t 7Hz), 2.29 (4H, m), 1.25 (12H, m) |
| Id-12 | 3-pyridyl | –CO–OH | 15 | Z | 2 | $C_{29}H_{41}NO_2$ Oil | 9.40 (COOH), 8.56 (2H, m), 8.46 (1H, d, 2Hz), 7.53 (1H, m), 7.20 (5H, m), 6.15 (1H, t, 7Hz), 2.33 (2H, m), 2.08 (2H, m), 1.25 (25H, m) |
| Id-13 | 3-pyridyl | –CO–OH | 15 | E | 2 | $C_{29}H_{41}NO_2$ Oil | 9.42 (COOH), 8.48 (2H, m), 7.53 (1H, m), 7.20 (5H, m), 6.12 (1H, t 7Hz), 2.28 (4H, m), 1.25 (26H, m) |

EXAMPLE 3

Ethyl (E)-7-phenyl-7-(3-pyridyl)-6-heptenoate (1.5 g, 4.8 mmoles) was dissolved in dry tetrahydrofuran (30 ml) and ice-cooled. Lithium aluminum hydride (0.5 g) was gradually added to the solution. The mixture was stirred at 0° C. for 30 minutes and a saturated aqueous Rochelle salt solution was added to precipiate the inorganic substance. The organic layer was separated and the precipitate was washed with tetrahydrofuran (30 ml). The tetrahydrofuran solutions were combined, dried over anhydrous magnesium sulfate and concentrated under reduced pressure. The residue was subjected to silica gel column chromatography using ethyl acetate as eluent to give (E)-7-phenyl-7-(3-pyridyl)-6-hepten-1-ol (1.2 g, 94%) (Compound Id-14) as an oil.

Compounds Id-15 to Id-18 produced by the above procedure of this example are listed in Table 3.

EXAMPLE 4

(Compound Id-17)

(E)-7-(3-Pyridyl)-7-(2-thienyl)-6-heptenoic acid (0.4 g, 1.4 mmoles) was dissolved in dry tetrahydrofuran (20 ml) and lithium aluminum hydride (0.1 g, 2.6 mmoles) was added to the solution. The mixture was stirred at 50° C. for an hour, followed by addition of a saturated aqueous Rochelle salt solution (10 ml). The organic alyer was separated and the precipitate was washed with tetrahydrofuran (20 ml). The tetrahydrofuran solutions were combined, dried over anhydrous magnesium sulfate and concentrated under reduced pressure. The residue was subjected to silica gel column chromatography using ethyl acetate as the eluent to give (E)-7-(3-pyridyl)-7-(2-thienyl)-6-hepten-1-ol (0.21 g, 52%) (Compound I-17).

Compounds Id-14, Id-15, Id-17 and Id-18 produced by the above procedure of this example are listed in Table 3.

TABLE 3

| Compound | R¹ | R²ᶜ | n | Isomer(s) | Prepared by the procedure of Example | Molecular formula (physical properties) | Nuclear magnetic resonance spectrum, δ values, TMS as internal standard |
|---|---|---|---|---|---|---|---|
| Id-14 | 3-pyridyl | CH₂OH | 4 | E | 3, 4 | $C_{18}H_{21}NO$ Oil | 8.48(1H, d, 2Hz), 8.40(1H, dd, 2Hz, 4Hz), 7.25(7H, m), 6.09 (1H, t, 7Hz), 3.58(2H, m), 2.14 (2H, m), 1.44(6H, m) |

TABLE 3-continued

| Compound | $R^1$ | $R^{2c}$ | n | Isomer(s) | Compound (Id) Prepared by the procedure of Example | Molecular formula (physical properties) | Nuclear magnetic resonance spectrum, δ values, TMS as internal standard |
|---|---|---|---|---|---|---|---|
| Id-15 | (phenyl) | CH₂OH | 4 | Z | 3, 4 | $C_{18}H_{21}NO$ Oil | 8.42(2H, m), 7.47(1H, m), 7.20 (6H, m), 6.16(1H, t, 7Hz), 3.59 (2H, m), 2.07(2H, m), 1.42(6H, m) |
| Id-16 | (phenyl) | CH₂OH | 3 | E + Z | 3 | $C_{17}H_{19}NO$ Oil | 8.44(2H, m), 7.30(7H, m), 6.16 (Z), 6.10(E)(1H, t, 7Hz), 3.58(2H, m), 2.10(2H, m), 1.50(4H, m) |
| Id-17 | (thienyl) | CH₂OH | 4 | E | 3, 4 | $C_{16}H_{19}NOS$ Oil | 8.56(1H, d, 2Hz), 8.46(2H, dd, 2Hz, 4Hz), 7.56(1H, dt, 2Hz, 7Hz), 7.25 (1H, m), 7.10(1H, m), 7.04(1H, m), 6.86(1H, m), 6.01(1H, m), 3.62(2H, m), 2.37(2H, m), 1.48(6H, m) |
| Id-18 | (thienyl) | CH₂OH | 4 | Z | 3, 4 | $C_{16}H_{19}NOS$ Oil | 8.49(2H, m), 7.57(1H, dt, 2Hz, 4Hz), 7.29(1H, dd, 4Hz, 7Hz), 7.12(1H, d, 4Hz), 6.84(1H, dd, 3Hz, 4Hz), 6.49 (1H, d, 3Hz), 6.22(1H, t, 7Hz), 3.56 (2H, m), 2.02(2H, m), 1.39(6H, m) |

EXAMPLE 5

(Compound Id-19)

(E)-7-Phenyl-7-(3-pyridyl)-6-hepten-1-ol (0.4 g, 1.5 mmoles) was dissolved in methylene chloride (10 ml) and pyridine (0.4 ml) and acetic anhydride (0.2 ml) were added to the solution. The mixture was allowed to stand at room temperature for 18 hours and then concentrated under reduced pressure. The residue was subjected to silica gel column chromatography using ethyl acetate as the developing solvent to give 1-acetoxy-(E)-7-phenyl-7-(3-pyridyl)-6-heptene (0.4 g, 86%) (Compound I-19) as an oil.

In the same manner as above, there was produced Compound Id-22.

EXAMPLE 6

(Compound Id-20)

(E)-7-Phenyl-7-(3-pyridyl)-6-hepten-1-ol (1.2 g, 4.5 mmoles) was added to formic acid (10 ml) and the mixture was refluxed for 7 hours. After cooling, the mixture was concentrated under reduced pressure and the resulting oil was subjected to silica gel column chromatography using isopropyl ether-ethyl acetate (1:1) as the eluent to give 1-formyloxy-(E)-7-phenyl-7-(3-pyridyl)-6-heptene (1.2 g, 91%) (Compound Id-20) as an oil.

EXAMPLE 7

(Compound Id-21)

(E)-7-Phenyl-7-(3-pyridyl)-6-hepten-1-ol (0.8 g, 3 mmoles) was dissolved in methylene chloride (10 ml), and pyridine (2 ml) and nicotinoyl chloride hydrochloride (0.55 g, 3 mmoles) were added. The mixture was stirred at room temperature for 18 hours and then concentrated under reduced pressure. The residue was subjected to silica gel column chromatography using isopropyl ether-ethyl acetate (1:1) as the developing solvent to give 1-nicotinyloxy-(E)-7-phenyl-7-(3-pyridyl)-6-heptene (1.0 g, 89.6%) (Compound Id-21) as an oil.

EXAMPLE 8

(Compound Id-23)

(E)-7-Phenyl-7-(3-pyridyl)-6-hepten-1-ol (2.0 g, 7.4 mmoles) was dissolved in methylene chloride (20 ml), and sodium cyanate (0.50 g, 7.7 mmoles) and trifluoroacetic acid (5 ml) were added. The mixture was stirred at room temperature for 20 hours and concentrated under reduced pressure. The residue was shaken with potassium carbonate (1 g), water (20 ml) and methylene chloride (50 ml), and the organic layer was separated, washed with water, dried and concentrated. Recrystallization of the residue from isopropyl ether gave 1-carbamoyloxy-(E)-7-(3-pyridyl)-6-heptene (1.82 g, 79%) (Compound Id-23).

EXAMPLE 9

(Compound Id-27)

(E)-7-Phenyl-7-(3-pyridyl)-6-hepten-1-ol (4 g, 15 mmoles) and phenyl isocyanate (1.6 ml, 15 mmoles) were dissolved in methylene chloride (20 ml), and triethylamine (0.5 ml) was added to the solution. The mixture was stirred at room temperature for 3 hours and then concentrated under reduced pressure. The residue was subjected to silica gel column chromatography using isopropyl ether-ethyl acetate (2:1) as the developing solvent and recrystallization of the product from a mixture of ethyl acetate and isopropyl ether gave 1-phenylaminocarbonyloxy-(E)-7-phenyl-7-(3-pyridyl)-6-heptene (3.2 g, 55%)

EXAMPLE 10

(Compound Id-24)

(E)-7-Phenyl-7-(3-pyridyl)-6-hepten-1-ol (2.0 g, 7.4 mmoles) was reacted with methyl isocyanate (500 mg, 8.8 mmoles) in the presence of triethylamine in the same manner as Example 9 to give 1-methylaminocarbonyloxy-(E)-7-phenyl-7-(3-pyridyl)-6-heptene (2.2 g) (Compound Id-24) as an oil. This compound forms a crystalline salt of oxalic acid.

EXAMPLE 11

(Compound Id-25)

In the presence of triethylamine, (E)-7-phenyl-7-(3-pyridyl)-6-hepten-1-ol (2.0 g, 7.4 mmoles) was reacted with n-butyl isocyanate (0.8 g) in the same manner as Example 9 to give 1-(n-butyl)aminocarbonyloxy-(E)-7-phenyl-7-(3-pyridyl)-6-heptene (Compound Id-25, 2.3 g) as an oil This product forms a crystalline salt of oxalic acid.

EXAMPLE 12

(Compound Id-28)

In the presence of triethylamine, (E)-7-phenyl-7-(3-pyridyl)-6-hepten-1-ol (2.0 g, 7.4 mmoles) was reacted with phenyl isothiocyanate (1.0 g, 7.5 mmoles) in the same manner as Example 9 to give 1-phenylaminothiocarbonyloxy-(E)-7-phenyl-7-(3-pyridyl)-6-heptene (Compound Id-28, 2.2 g) as crystals.

EXAMPLE 13

(Compound Id-29)

(E)-7-Phenyl-7-(3-pyridyl)-6-hepten-1-ol (2.0 g, 7.4 mmoles) was dissolved in methylene chloride (20 ml), and p-toluenesulfonyl isocyanate (1.5 g, 7.6 mmoles) was added to the solution. The mixture was stirred at room temperature for an hour and then concentrated under reduced pressure. The residue was subjected to silica gel column chromatography using isopropyl ether-ethyl acetate (1:1) as the developing solvent. Recrystallization of the product from ethyl acetate gave 1-(p-toluenesulfonyl)aminocarbonyloxy-(E)-7-phenyl-7-(3-pyridyl)-6-heptene (2.1 g, 60%) (Compound Id-29).

TABLE 4

| Compound | $R^1$ | $R^{2c}$ | n | Isomer(s) | Prepared by the procedure of Example | Molecular formula (physical properties) | Nuclear magnetic resonance spectrum, δ values, TMS as internal standard |
|---|---|---|---|---|---|---|---|
| Id-19 | 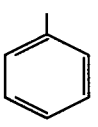 | −CH₂−O−CO−CH₃ | 4 | E | 5 | $C_{20}H_{23}NO_2$ Oil | 8.47(1H,d,2Hz), 8.43(1H,dd, 2Hz,4Hz), 7.30(7H,m), 6.09 (1H,t,7Hz), 4.02(2H,m), 2.10(2H,m), 2.01(3H,s), 1.43 (6H,m) |
| Id-20 | 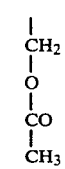 | −CH₂−O−CHO | 4 | E | 6 | $C_{19}H_{21}NO_2$ Oil | 8.50(1H,d,2Hz), 8.42(1H,d, 4Hz), 8.01(1H,s), 7.33(7H,m), 6.09(1H,t,7Hz), 4.14(2H,t, 7Hz), 2.17(2H,m), 1.44(6H,m) |
| Id-21 | 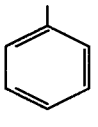 | −CH₂−O−CO−(3-pyridyl) | 4 | E | 7 | $C_{24}H_{24}N_2O_2$ Oil | 9.23(1H,d,2Hz), 8.78(1H,dd, 2Hz,5Hz), 8.54(1H,d,2Hz), 8.46(1H,dd,2Hz,4Hz), 8.29(1H, dt,2Hz,7Hz), 7.30(8H,m), 6.12 (1H,t,7Hz), 4.32(2H,t,7Hz), 2.19(2H,m), 1.57(6H,m) |
| Id-22 | 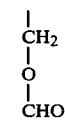 | −CH₂−O−CO−CH₃ | 4 | E | 6 | $C_{18}H_{21}NO_2S$ Oil | 8.56(1H,d,2Hz), 8.46(2H,dd,2Hz, 4Hz), 7.55(1H,dt,2Hz,7Hz), 7.25 (1H,m), 7.10(1H,m), 7.04(1H,m), 6.86(1H,m), 6.01(1H,m), 4.01(2H, m), 2.02(3H,s), 1.43(6H,m) |
| Id-23 | 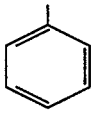 | −CH₂−O−CO−NH₂ | 4 | E | 8 | $C_{19}H_{22}N_2O_2$ 50–51° C. | 8.51(1H,d,2Hz), 8.42(1H,dd, 2Hz,4Hz), 7.31(7H,m), 6.08 (1H,t,7Hz), 4.88(2H,m), 4.01(2H,t,8Hz), 2.10(2H,m), 1.43(6H,m) |

TABLE 4-continued

Compound (Id)

| Compound | R¹ | R²ᶜ | n | Isomer(s) | Prepared by the procedure of Example | Molecular formula (physical properties) | Nuclear magnetic resonance spectrum, δ values, TMS as internal standard |
|---|---|---|---|---|---|---|---|
| Id-24 | phenyl | —CH₂—O—CO—NH—CH₃ | 4 | E | 9,10 | $C_{22}H_{26}N_2O_6$ 97–98° C. Oil | *8.50(1H,d,2Hz), 8.42(1H,dd,2Hz,4Hz), 7.32(7H,m), 6.09(1H,t,7Hz), 4.79(NH), 4.02(2H,t,8Hz), 2.74 (3H,d,4Hz), 2.16(2H,m), 1.42(6H,m) |
| Id-25 | phenyl | —CH₂—O—CO—NH—nBu | 4 | E | 11 | $C_{25}H_{32}N_2O_6$ 85–86° C. Oil | *8.51(1H,d,2Hz), 8.44(1H,dd,2Hz,4Hz), 7.32(7Hz,m), 6.10 (1H,t,7Hz), 4.70(NH), 4.01(2H,t,8Hz), 3.16(2H,m), 2.19(2H,m), 1.09(10H,m), 0.90(3H,t) |
| Id-26 | thienyl | —CH₂—O—CO—NH—CH₃ | 4 | E | 9,10 | $C_{18}H_{22}N_2O_2S$ Oil | 8.56(1H,d,2Hz), 8.46(2H,dd,2Hz,4Hz), 7.56(1H,dt,2Hz,7Hz), 7.25(1H,m), 7.10 (1H,m), 7.04(1H,m), 6.86(1H,m), 6.01 (1H,m), 4.82(NH), 4.02(2H,t,8Hz), 2.74 (3H,d,4Hz), 2.16(2H,m), 1.42(6H,m) |
| Id-27 | phenyl | —CH₂—O—CO—NH—phenyl | 4 | E | 9 | $C_{25}H_{26}N_2O_2$ 92–93° C. | 8.51(1H,d,2Hz), 8.42(1H,dd, 2Hz,4Hz), 7.27(12H,m), 6.08 (1H,t,7Hz), 4.09(2H,t,8Hz), 2.18(2H,m), 1.43(6H,m) |
| Id-28 | phenyl | —CH₂—O—CS—NH—phenyl | 4 | E | 12 | $C_{25}H_{28}N_2O_5S$ 105–108° C. (As oxalate) | *8.52(1H,d,2Hz), 8.44(1H,dd, 2Hz,4Hz), 7.32(12H,m), 6.08 (1H,t,7Hz), 4.53(2H,t,8Hz), 2.16(2H,m), 1.46(6H,m) |

TABLE 4-continued

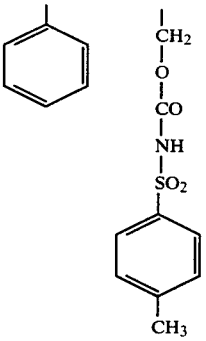

| Compound | R¹ | R²c | n | Isomer(s) | Prepared by the procedure of Example | Molecular formula (physical properties) | Nuclear magnetic resonance spectrum, δ values, TMS as internal standard |
|---|---|---|---|---|---|---|---|
| Id-29 | | —CH₂—O—CO—NH—SO₂—C₆H₄—CH₃ | 4 | E | 13 | $C_{26}H_{28}N_2O_4S$ 147–148° C. | 8.52(1H,d,2Hz), 8.42(1H,dd, 2Hz,4Hz), 7.89(2H,d,8Hz), 7.39(9H,m), 6.06(1H,t,7Hz), 4.01(2H,t,8Hz), 2.40(3H,s), 2.11(2H,m), 1.34(6H,m) |

*Data obtained with the free base

EXAMPLE 14

(Compound Id-5)

p-Toluenesulfonate of (E)-7-phenyl-7-(3-pyridyl)-6-hepten-1-ol (0.45 g, 1.07 mmoles) was dissolved in hexamethylphosphoramide (2 ml), and sodium iodide (0.2 g, 1.3 mmoles) was added to the solution. The mixture was stirred for 10 minutes. To the mixture was added sodium cyanoborohydride (0.1 g, 16 mmoles) and the resulting mixture was stirred at 100° C. for an hour. The reaction mixture was then cooled and water (10 ml) was added followed by extraction of the product with ethyl acetate. The organic layer was washed with water, dried and concentrated under reduced pressure. The residue was subjected to silica gel column chromatography using isopropyl ether-ethyl acetate (4:1) as the eluent to give (E)-1-phenyl-1-(3-pyridyl)-1-heptene (0.2 g, 75%) as an oil.

(E)-1-Phenyl-1-(3-pyridyl)-1-heptene was also obtained by reduction of the above p-tluenesulfonate with lithium aluminum hydride in tetrahydrofuran.

In the same manner as above, there were produced Compounds Id-1 to Id-7.

EXAMPLE 15

(Compound Id-30)

p-Toluenesulfonate of (E)-7-phenyl-7-(3-pyridyl)-6-hepten-1-ol (15 g, 36 mmoles) and sodium iodide (18 g, 120 mmoles) were dissolved in acetone (100 ml) and the solution was stirred at room temperature for 3 hours. Water (200 ml) was added to the mixture and the product was extracted twice with ethyl ether. The organic layer was washed with water, dried (magnesium sulfate) and concentrated under reduced pressure to give (E)-1-iodo-7-phenyl-7-(3-pyridyl)-6-heptene (13 g, 96%) as an oil.

In the same manner as this example, Compound I-31 was produced.

EXAMPLE 16

(Compound Id-32)

(E)-1-Iodo-7-phenyl-7-(3-pyridyl)-6-heptene (3.7 g, 10 mmoles) was dissolved in acetonitrile (100 ml), and silver nitrate (5 g, 30 mmoles) was added to the solution. The mixture was stirred at room temperature. After 3 hours, water (100 ml) and ethyl acetate (100 ml) were added and the insoluble matter was filtered off. The filtrate was concentrated under reduced pressure and the residue was dissolved in ethyl acetate. The organic layer was washed with water, dried (magnesium sulfate) and concentrated under reduced pressure. The residue was then subjected to silica gel column chromatography using isopropyl ether-ethyl acetate (1:1) as the eluent to give 1-nitroxy-(E)-7-phenyl-7-(3-pyridyl)-6-heptene (2.5 g, 80%) (Compound Id-32) as an oil. The oxalic acid salt of this product was recrystallized from acetone.

Compounds Id-33 and Id-34 produced by the same procedure as above are listed in Table 5.

TABLE 5

| Compound | R¹ | R²c | n | Isomer(s) | Prepared by the procedure of Example | Molecular formula (physical properties) | Nuclear magnetic resonance spectrum, δ values, TMS as internal standard |
|---|---|---|---|---|---|---|---|
| Id-30 | phenyl | —CH₂—I | 4 | E | 15 | $C_{18}H_{20}NI$ Oil | 8.51(1H, d, 2Hz), 8.40(1H, dd, 2Hz, 4Hz), 7.32(7H, m), 6.08(1 H, t, 7Hz), 3.11(2H, t, 8Hz), 2.17(2H, m), 1.45(6H, m) |

TABLE 5-continued

| Compound | R$^1$ | R$^{2c}$ | n | Isomer(s) | Prepared by the procedure of Example | Molecular formula (physical properties) | Nuclear magnetic resonance spectrum, δ values, TMS as internal standard |
|---|---|---|---|---|---|---|---|
| Id-31 | (2-methyl-thiophene) | —CH$_2$—I | 4 | E | 15 | C$_{16}$H$_{18}$INS Oil | 8.54(1H, d, 2Hz), 8.44(2H, dd, 2Hz, 4Hz), 7.54(1H, dt, 2Hz, 7Hz), 7.23 (1H, m), 7.08(1H, m), 7.02(1H, m), 6.84(1H, m), 6.06(1H, m), 3.12(2H, t, 8Hz), 2.16(2H, m), 1.44(6H, m) |
| Id-32 | (p-methylphenyl) | —CH$_2$ONO$_2$ | 4 | E | 16 | C$_{20}$H$_{22}$N$_2$O$_7$ 109–110° C. (As oxalate) | *8.51(1H, d, 2Hz), 8.43(1H, dd, 2Hz, 4Hz), 7.33(7H, m), 6.08(1H, t, 7Hz), 4.39(2H, t, 8Hz), 2.11 (2H, m), 1.46(6H, m) |
| Id-33 | (2-methyl-thiophene) | —CH$_2$ONO$_2$ | 4 | E | 16 | C$_{16}$H$_{18}$N$_2$O$_3$S Oil | 8.56(1H, d, 2Hz), 8.46(2H, dd, 2Hz, 4Hz), 7.56(1H, dt, 2Hz, 7Hz), 7.24 (1H, m), 7.10(1H, m), 7.04(1H, m), 6.86(1H, m), 6.04(1H, m), 4.39(2H, t, 8Hz), 2.12(2H, m), 1.45(6H, m) |
| Id-34 | (3,4-methylenedioxy-phenyl with methyl) | —CH$_2$ONO$_2$ | 4 | Z | 16 | C$_{19}$H$_{20}$N$_2$O$_4$ Oil | 8.50(2H, m), 7.47(2H, m), 6.80(1H, d, 8Hz), 6.60(1H, dd, 2Hz, 8Hz), 6.57(1H, d, 2Hz), 6.06(1H, t, 7Hz), 5.96(2H, s), 4.38(2H, t, 8Hz), 2.12 (2H, m), 1.46(6H, m) |

*Data obtained with the free base

EXAMPLE 17

(Compound Id-35)

Oxalyl chloride (0.3 ml) was added to methylene chloride (10 ml) and the mixture was cooled to −60° C., followed by dropwise addition of a methylene chloride solution (10 ml) containing dimethyl sulfoxide (0.6 ml). After stirring at the same temperature for 10 minutes, a solution of (E+Z)-6-phenyl-6-(3-pyridyl)-5-hexen-1-ol (0.7 g, 2.7 mmoles) in methylene chloride (5 ml) was added, and the mixture was stirred for 10 minutes. And then, triethylamine (3 ml) was added and the temperature was gradually raised to room temperature. Water (50 ml) was added and the product was extracted with ethyl acetate. The organic layer was washed with water, dried and concentrated under reduced pressure and the residue was subjected to silica gel column chromatography using isopropyl ether-ethyl acetate (1:1) as the eluent to give (E+Z)-1-formyl-5-phenyl-5-(3-pyridyl)-4-pentene (0.5 g, 70%) (Compound Id-35) as an oil.

In the same manner as above, Compound Id-36 was produced.

EXAMPLE 18

(Compound Id-37)

p-Toluenesulfonate of (E)-7-phenyl-7-(3-pyridyl)-6-hepten-1-ol (0.2 g, 0.5 mmole) was dissolved in a methanolic solution (1 ml) of 28% sodium methoxide and the solution was allowed to stand at room temperature for 3 days. To the reaction mixture was added water (10 ml) and the product was extracted twice with ethyl acetate. The organic layer was washed with water, dried and concentrated under reduced pressure. The residue was then subjected to silica gel column chromatography using isopropyl ether-ethyl acetate (1:1) as the developing solvent to give (E)-1-methoxy-7-phenyl-7-(3-pyridyl)-6-heptene (0.1 g, 75%) (Compound I-37) as an oil.

EXAMPLE 19

(Compound Id-38)

(E)-1-Iodo-7-phenyl-7-(3-pyridyl)-6-heptene (0.6 g, 1.6 mmoles) and phenol (0.2 g, 2.1 mmoles) were dissolved in a mixture of tetrahydrofuran (10 ml) and dimethylformamide (2 ml), and sodium hydride (60% dispersion in oil, 0.1 g, 2.5 mmoles) was added to the solution. The mixture was stirred at room temperature for 1.5 hours. To the reaction mixture was added water (20 ml), followed by extraction of the product with ether. The organic layer was washed with water, dried and concentrated under reduced pressure. The residue was then subjected to silica gel column chromatography using isopropyl ether-ethyl acetate (2.1) as the developing solvent to give (E)-1-phenoxy-7-phenyl-7-(3-pyridyl)-6-heptene (0.5 g, 73%) (Compound Id-38) as an oil.

EXAMPLE 20

(E)-7-Phenyl-7-(3-pyridyl)-6-hexen-1-ol (1.0 g, 3.7 mmoles) was dissolved in methylene chloride, and 3,4-dihydro-α-pyran (0.6 ml) and then D-camphorsulfonic acid (1.4 g, 6 mmoles) were added to the solution, followed by stirring at room temperature. After 1 hour, saturated aqueous sodium hydrogen carbonate was added, and the product was extracted with ethyl acetate. The organic layer was washed with water, dried and concentrated under reduced pressure to give (E)-7-phenyl-1-(2-pyranyloxy)-7-(3-pyridyl)-6-hexene (1.28 g, 90%) (Compound Id-39) as an oil.

EXAMPLE 21

(Compound Id-40)

(E+Z)-1-Iodo-6-phenyl-6-(3-pyridyl)-5-hexene (0.38 g, 0.83 mmole) and imidazole (0.2 g, 3 mmoles) were dissolved in dimethylformamide (10 ml), and sodium hydride (60% in oil, 0.2 g, 5 mmoles) was added to the solution. The mixture was stirred at room temperature for an hour. To the reaction mixture was added water (10 ml), and the product was extracted with ethyl acetate. The organic layer was washed with water, dried and concentrated under reduced pressure, and the residue was subjected to silica gel column chromatography using ethanol-ethyl acetate-triethylamine (1:20:0.1) as the eluent to give (E+Z)-1-(1-imidazolyl)-6-phenyl-6-(3-pyridyl)-5-hexene (0.25 g, 95%) as an oil.

Compounds Id-41 and Id-42 produced by the same procedure as above are listed in Table 6.

TABLE 6

Compound (Id)

| Compound | $R^1$ | $R^{2c}$ | n | Isomer(s) | Prepared by the procedure of Example | Molecular formula (physical properties) | Nuclear magnetic resonance spectrum, δ values, TMS as internal standard |
|---|---|---|---|---|---|---|---|
| Id-35 | phenyl | CHO | 3 | E + Z | 17 | $C_{17}H_{17}NO$ Oil | 9.70(1H, s), 8.48(2H, m), 7.20 (7H, m), 6.13 and 6.07(1H, t, 7Hz), 2.37(2H, m), 2.13(2H, m), 1.78(2H, m) |
| Id-36 | phenyl | CHO | 4 | E | 17 | $C_{18}H_{19}NO$ Oil | 9.68(1H, s), 8.48(1H, d, 2Hz), 8.40(1H, dd, 2Hz, 4Hz), 7.25(7 H, m), 6.10(1H, t, 7Hz), 2.37(2 H, m), 2.10(2H, m), 1.65(4H, m) |
| Id-37 | phenyl | —CH₂OCH₃ | 4 | E | 18 | $C_{19}H_{23}NO$ 87–88° C. (As oxalate) | *8.51(1H, d, 2Hz), 8.40(1H, dd, 2Hz, 4Hz), 7.32(7H, m), 6.11(1 H, t, 7Hz), 3.32(2H, t, 8Hz), 3.28(3H, s), 2.10(2H, m), 1.41 6H, m) |
| Id-38 | phenyl | —CH₂—O—phenyl | 4 | E | 19 | $C_{24}H_{25}NO$ Oil | 8.51(1H, d, 2Hz), 8.43(1H, dd, 2Hz, 4Hz), 7.14(12H, m), 6.10 (1H, t, 7Hz), 3.89(2H, t, 8Hz), 2.13(2H, m), 1.50(6H, m) |
| Id-39 | phenyl | —CH₂—O—tetrahydropyranyl | 4 | E | 20 | $C_{23}H_{29}NO_2$ Oil | 8.49(1H, d, 2Hz), 8.41(1H, dd, 2Hz, 4Hz), 7.19(7H, m), 6.08(1 H, t, 7Hz), 4.53(1H, s), 3.63(4 H, m), 2.19(2H, m), 1.49(12H, m) |
| Id-40 | phenyl | —CH₂—N(imidazolyl) | 3 | E + Z | 21 | $C_{20}H_{21}N_3$ Oil | 8.46(2H, m), 7.25(9H, m), 6.83 (1H, m), 6.11(Z), 6.04(E)(1H, t, 7Hz), 3.84(2H, m), 2.14(2H, m), 1.76(2H, m), 1.44(2H, m) |
| Id-41 | phenyl | —CH₂—N(triazolyl) | 3 | E + Z | 21 | $C_{19}H_{20}N_4$ Oil | 8.46(2H, m), 7.93(2H, m), 7.25(7 H, m), 6.11(Z), 6.04(E)(1H, t, 7Hz), 4.08(2H, m), 2.18(2H, m), 1.84 (2H, m), 1.40(2H, m) |
| Id-42 | phenyl | —CH₂—N(tetrazolyl) | 3 | E + Z | 21 | $C_{18}H_{19}N_5$ Oil | 8.47(2H, m), 7.92(1H, m), 7.25 (7H, m), 6.11(Z), 6.04(E)(1H, t, 7Hz), 4.09(2H, t, 7Hz), 2.16(2H, m), 1.89(2H, m), 1.46(2H, m) |

*Data obtained with the free base.

EXAMPLE 22

(Compound Id-43)

(E)-7-Phenyl-7-(3-pyridyl)-6-heptenoic acid (0.56 g, 2 mmoles) was dissolved in oxalyl chloride (5 ml), and the solution was heated at 50° C. for an hour. After concentration under reduced pressure, 5% ammonia-methanol (5 ml) was added and the mixture was allowed to stand at room temperature for an hour. The methanol was removed under reduced pressure and the residue was recrystallized from isopropyl ether to give (E)-7-phenyl-7-(3-pyridyl)-6-heptenamide (0.48 g).

EXAMPLE 23

(Compound Id-44)

To (E)-7-phenyl-7-(3-pyridyl)-6-heptenoyl chloride hydrochloride (0.67 g, 2 mmoles) as produced in Example 22 were added a methylene chloride solution (20 ml) containing aniline (200 mg) and potassium carbonate (300 mg), and the mixture was stirred at room temperature for 4 hours. To the reaction mixture was added water and, after washing with water, the methylene chloride solution was dried and concentrated. The residue was then recrystallized from ethyl acetate to give N-phenylamide of (E)-7-phenyl-7-(3-pyridyl)-6-heptenoic acid (620 mg) (Compound Id-44).

EXAMPLE 24

(Compound Id-45)

p-Toluensulfonate of (E)-7-phenyl-7-(3-pyridyl)-6-hepten-1-ol (1.0 g, 2.4 mmoles) was dissolved in dimethyl sulfoxide (10 ml), and sodium cyanide (0.3 g, 6 mmoles) was added, followed by stirring for 18 hours. To the reaction mixture was added water (100 ml) and the product was extracted with ethyl acetate. The organic layer was washed with water, dried and concentrated under reduced pressure. The residue was subjected to silica gel column chromatography using ethyl acetate-isopropyl ether (1:1) as the developing solvent to give (E)-1-cyano-7-phenyl-7-(3-pyridyl)-6-heptene (0.5 g, 76%).

EXAMPLE 25

(Compound Id-46)

(E)-7-Phenyl-7-(3-pyridyl)-6-hepten-1-ol (2.3 g, 8.6 mmoles) was dissolved in methylene chloride (2.0 ml), and pyridine (1 ml) and p-toluenesulfonyl chloride (1.8 g, 9.4 mmoles) were added. The reaction was allowed to proceed at room temperature overnight, and water (30 ml) was added, followed by extraction of the product with ethyl acetate. The organic layer was washed with water and dried and the solvent was distilled off. The resulting oily product was subjected to silica gel column chromatography using isopropyl ether-ethyl acetate (1:1) as the eluent to give p-toluensulfonate of (E)-7-phenyl-7-(3-pyridyl)-6-hepten-1-ol (3.15 g, 88%) as an oil.

In the same manner as above, Compound Id-47 was prepared.

EXAMPLE 26

(Compound Id-48)

(E)-7-Phenyl-7-(3-pyridyl)-6-hepten-1-ol (1.0 g, 3.7 mmoles) and imidazole (0.25 g, 3.7 mmoles) were dissolved in dimethylformamide (10 ml), and dimethyl-t-butylsilyl chloride (0.55 g, 3.7 mmoles) was added, followed by stirring for an hour. To the reaction mixture was added water (20 ml) and the product was extracted with ethyl acetate. The organic layer was washed with water and dried and the solvent was distilled off under reduced pressure. The residue was subjected to silica gel column chromatography using isopropyl ether-ethyl acetate (1:1) as the developing solvent to give dimethyl-t-butylsilyl ether of (E)-7-phenyl-7-(3-pyridyl)-6-hepten-1-ol (1.1 g, 84%) as an oil.

TABLE 7

| | | | | Compound (Id) | | |
|---|---|---|---|---|---|---|
| Compound | $R^1$ | $R^{2c}$ | n | Isomer(s) | Prepared by the procedure of Example | Molecular formula (physical properties) | Nuclear magnetic resonance spectrum, δ values, TMS as internal standard |
| Id-43 | phenyl | –CO–NH$_2$ | 4 | E | 22 | $C_{18}H_{20}N_2O$ 97–98° C. | 8.45(2H,m),7.26(7H,m), 6.08(1H,t,7Hz),5.50(2H,NH$_2$), 2.15(4H,m),1.57(4H,m) |
| Id-44 | phenyl | –CO–NH–phenyl | 4 | E | 23 | $C_{24}H_{24}N_2O$ 125–126° C. | 8.46(1H,d,2Hz),8.40(1H,dd, 2Hz,4Hz),7.27(12H,m),6.06 (1H,t,7Hz),2.22(4H,m),1.62 (4H,m) |
| Id-45 | phenyl | CN | 5 | E | 24 | $C_{19}H_{20}N_2$ Oil | 8.49(1H,d,2Hz),8.42(1H,dd, 2Hz,4Hz),7.32(7H,m),6.06 (1H,t,7Hz),2.26(4H,m),1.48 (6H,m) |

TABLE 7-continued

| Compound | R¹ | R²c | n | Isomer(s) | Prepared by the procedure of Example | Molecular formula (physical properties) | Nuclear magnetic resonance spectrum, δ values, TMS as internal standard |
|---|---|---|---|---|---|---|---|
| Id-46 | 4-methylphenyl | –CH₂–O–SO₂–(4-methylphenyl) | 4 | E | 25 | $C_{25}H_{27}NO_3S$ Oil | 8.48(1H,d,2Hz),8.43(1H,dd,2Hz,4Hz),7.76(2H,d,8Hz),7.32(9H,m),6.03(1H,t,7Hz),3.93(2H,t,8Hz),2.40(3H,s),2.10(2H,m),1.37(6H,m) |
| Id-47 | 2-methylthienyl | –CH₂–O–SO₂–(4-methylphenyl) | 4 | E | 25 | $C_{23}H_{25}NO_3S_2$ Oil | 8.56(1H,d,2Hz),8.46(2H,dd,2Hz,4Hz),7.77(2H,d,8Hz),7.55(1H,dt,2Hz,7Hz),7.30(3H,m),7.10(1H,m),7.04(1H,m),6.86(1H,m),6.02(1H,m),3.95(2H,t,8Hz),2.40(3H,s),2.10(2H,m),1.37(6H,m) |
| Id-48 | 4-methylphenyl | –CH₂–O–Si(CH₃)₂–tBu | 4 | E | 26 | $C_{24}H_{35}NOSi$ Oil | 8.49(1H,d,2Hz),8.40(1H,dd,2Hz,4Hz),7.28(7H,m),6.07(1H,t,7Hz),3.53(2H,t,7Hz),2.12(2H,m),1.37(6H,m),0.82(9H,s),0.05(6H,s) |

REFERENCE EXAMPLE 1

To dimethylsulfoxide (40 ml) was added dropwise sodium hydride (1.0 g), and the mixture was heated at 80° C. for 30 minutes. The reaction mixture was cooled to room temperature, to which was added 5-carboxypentyltriphenyl phosphonium bromide (9.5 g, 21 mmole), and the mixture was stirred for 5 minutes. To the reaction mixture was added a tetrahydrofuran solution (10 ml) of 3.7 g (0.02 mole) of 3-benzoylpyridine. The mixture was stirred for 30 minutes at room temperature, followed by addition of water (100 ml), which was subjected to extraction twice with ethylacetate (50 ml). The aqueous layers were combined and adjusted to pH 6 with 2N HCl, which was subjected to extraction with ethyl acetate. The organic layers were combined and washed with water and dried (magnesium sulfate). The solvent was then evaporated and the residue was subjected to a silica-gel chromatography using ethanol-ethyl acetate (1:5) as the eluent to yield (E)+(Z)-7-(3-pyridyl)-7-phenyl-6-heptenoic acid (A-3, I-4 in Table 10) (4.5 g 79%).

By the procedure analogous to the above Example, A-1, A-2, A-4 and A-5 in Table 10 were prepared.

Separation of isomers was conducted by means of fractional crystallization or a liquid chromatography using Lobar Lichroprep RP-8 (40–63 μm, manufactured by Merck & Co.).

TABLE 10

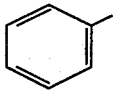

| | | | Compound (A) | |
|---|---|---|---|---|
| Compound | $R^1$ | n | Isomer(s) (melting point) | Nuclear magnetic resonance spectrum, δ values, TMS as internal standard |
| A-1 | 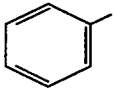 | 3 | Z | 11.1(1H,COOH),8.53(1H,m),8.45(1H,m), 7.20(7H,m),6.17(1H,t,7Hz),2.32(2H,m), 2.17(2H,m),1.79(2H,m) |
| A-2 | 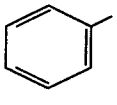 | 3 | E | 11.1(1H,COOH),8.53(1H,m),8.45(1H,m), 7.20(7H,m),6.12(1H,t,7Hz),2.32(2H,m), 2.17(2H,m),1.79(2H,m) |
| A-3 | 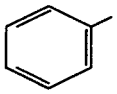 | 4 | Z | 11.6(1H,COOH),8.53(1H,m),8.46(1H,m), 7.54(1H,d,7Hz),7.27(6H,m),6.16(1H,t, 7Hz),2.29(2H,t,7Hz),2.17(2H,m),1.57 (4H,m) |
| A-4 | 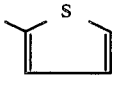 | 4 | E 108–110° C. | 11.8(1H,COOH),8.55(2H,m),7.46(1H,d,7 Hz),7.31(3H,m),7.16(3H,m),6.13(1H,t, 7Hz),2.29(2H,t,7Hz),2.13(2H,t,7Hz), 1.58(4H,m) |
| A-5 | 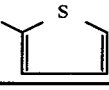 | 4 | E (84–85° C.) | 10.50(1H,COOH),8.59(1H,d,2Hz),8.48(1H,d,d, 2 & 4Hz),7.58(1H,d,t,7 & 2Hz),7.29(1H,m), 7.24(1H,d,d,4 & 7Hz),7.04(1H,m),6.85(1H,m), 6.04(1H,t,8Hz),2.34(4H,m),1.64(4H,m) |
| A-6 | 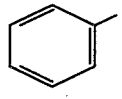 | 4 | Z (93–94° C.) | 11.90(1H,COOH),8.53(2H,m),7.62(1H,m), 7.20(1H,m),7.15(1H,m),6.85(1H,m),6.48 (1H,m),6.22(1H,t,7Hz),2.35(4H,m), 1.63(4H,m) |

TABLE 8

| | | | | Compound (Ie) | |
|---|---|---|---|---|---|
| Compound | $R^1$ | $R^{2c}$ | n Isomer(s)* | Molecular formula (physical properties) | Nuclear magnetic resonance spectrum, δ values, TMS as internal standard |
| Ie-1 | 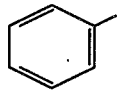 | —COOH | 2 E | $C_{16}H_{15}NO_3$ 175–176° C. | 10.40 (1H), 8.32 (1H), 8.19 (1H), 7.23 (7H), 8.29 (1H), 2.41 (4H) |
| Ie-2 | 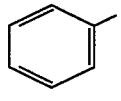 | —COOH | 4 E | $C_{18}H_{19}NO_3$ 166–167° C. | 8.28 (1H), 8.17 (1H), 7.26 (7H), 6.22 (1H), 2.28 (2H), 2.16 (2H), 1.58 (4H) |
| Ie-3 | 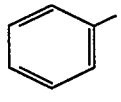 | —COOH | 4 Z | $C_{18}H_{19}NO_3$ 141–142° C. | 8.29 (1H), 8.21 (1H), 7.60 (1H), 7.29 (7H), 6.18 (1H), 2.19 (4H), 1.56 (4H) |
| Ie-4 | 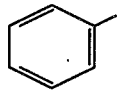 | —COOH | 9 E | $C_{23}H_{29}NO_3$ 102–103° C. | 8.34 (1H), 8.14 (1H), 7.24 (7H), 6.22 (1H), 2.31 (4H), 1.27 (14H) |

TABLE 8-continued

| Compound | R¹ | R²c | n Isomer(s)* | Molecular formula (physical properties) | Nuclear magnetic resonance spectrum, δ values, TMS as internal standard |
|---|---|---|---|---|---|
| Ie-5 | 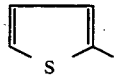 (thiophene) | —COOH | 4 E | $C_{16}H_{17}NO_3S$ 147–148° C. | 8.31 (1H), 8.22 (1H), 7.50 (1H), 7.25 (3H), 7.05 (1H), 6.88 (1H), 6.15 (1H), 2.30 (4H), 1.62 (4H) |
| Ie-6 | 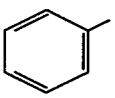 (phenyl) | —COOMe | 4 E | $C_{19}H_{21}NO_3$ Oil | 8.08 (2H), 7.28 (7H), 6.16 (1H), 3.64 (3H), 2.17 (4H), 1.88 (4H) |
| Ie-7 | 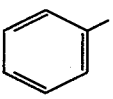 (phenyl) | $CH_2$—OH | 4 E | $C_{18}H_{21}NO_2$ Oil | 8.09 (2H), 7.28 (7H), 6.17 (1H), 3.57 (2H), 2.16 (2H), 1.41 (6H) |
| Ie-8 | 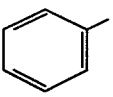 (phenyl) | $CH_2$—OCNH—phenyl | 4 E | $C_{25}H_{26}N_2O_3$ Oil | 8.12 (2H), 7.35 (12H), 6.15 (1H), 4.11 (2H), 2.08 (2H), 1.43 (6H) |
| Ie-9 | 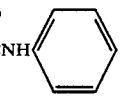 (phenyl) | $CH_3$ | 4 E | $C_{18}H_{21}NO$ Oil | 8.08 (2H), 7.28 (7H), 6.17 (1H), 2.11 (2H), 1.28 (6H), 0.81 (3H) |

*Compound in formula (I), in which pyridyl group combined with the carbon atom at one side of the olefinic bond and the hydrogen atom combined with the carbon atom at the other side of the olefinic bond exist in the same direction, is shown as E isomer, and compound, in which the pyridyl group and the hydrogen atom exist in the opposite direction, is shown as Z isomer.

EXAMPLE 29

(A) Capsule

| | |
|---|---|
| (1) Compound Id-52 | 50 mg |
| (2) Cellulose fine powder | 30 mg |
| (3) Lactose | 37 mg |
| (4) Magnesium stearate | 3 mg |
| Total | 120 mg |

All the materials were mixed and filled into a gelatin capsule.

(B) Soft Capsule

| | |
|---|---|
| (1) Compound Id-68 | 50 mg |
| (2) Cor starch oil | 100 mg |
| Total | 150 mg |

A mixed solution of (1) and (2) were prepared and filled into a soft capsule by a conventional manner.

(C) Tablet

| | |
|---|---|
| (1) Compound Id-52 | 50 mg |
| (2) Lactose | 34 mg |
| (3) Corn starch | 10.6 mg |
| (4) Corn starch (gelatinized) | 5 mg |
| (5) Magnesium stearate | 0.4 mg |
| (6) Calcium carboxymethyl cellulose | 20 mg |

All the materials were mixed and compressed by a tabletting machine to prepare a tablet in accordance with a conventional manner.

EXPERIMENTAL EXAMPLE 1

Inhibitory effect on blood thromboxane $A_2$ ($TXA_2$) production in rats

Male Sprague-Dawley rats aged 7 to 8 weeks were used in groups of 5 individuals. Rats in the dosing group received by oral administration of 2 ml/kg of an aqueous suspension of 10 mg/kg of the test compound prepared with a small amount of gum arabic. To rats in the control group, a suspension of gum arabic only was similarly administered. Two hours after administration, each rat was anesthetized with pentobarbital sodium (50 mg/kg, intraperitoneal) and 1 ml of blood was taken from the abdominal aorta. The blood was allowed to stand at 25° C. for 90 minutes, after which it was centrifuged at 15,000 rpm for 2 minutes to separate the serum. The serum thromboxane $B_2$ ($TXB_2$) which was a stable metabolite of $TXA_2$ produced in the blood during the standing procedure was determined by radioimmunoassay (Shibouta et al., Biochemical Pharmacol. 28, 3601, 1979). The percent inhibition of $TXA_2$ synthetase was calculated from the difference in $TXB_2$ production between the control and dosing groups.

The results for some representative compounds are shown in Table 9.

TABLE 9

| Compound | % inhibition of $TXA_2$ synthetase | Compound | % inhibition of $TXA_2$ synthetase |
|---|---|---|---|
| Id-5 | 73 | Id-9 | 90 |
| Id-14 | 92 | Id-15 | 87 |
| Id-17 | 95 | Id-18 | 72 |
| Id-19 | 94 | Id-20 | 87 |
| Id-24 | 90 | Id-25 | 83 |
| Id-27 | 87 | Id-28 | 79 |
| Id-29 | 94 | Id-32 | 94 |

TABLE 9-continued

| Compound | % inhibition of TXA$_2$ synthetase | Compound | % inhibition of TXA$_2$ synthetase |
|---|---|---|---|
| Id-37 | 92 | Id-43 | 93 |
| Id-44 | 94 | Id-48 | 91 |
| Ie-2 | 85 | Ie-3 | 70 |
| Ie-4 | 85 | Ie-5 | 90 |
| Ie-6 | 80 | Ie-7 | 80 |
| Ie-8 | 80 | Ie-9 | 68 |

EXAMPLE 27

(E)-7-phenyl-7-(3-pyridyl)-6-heptenoic acid (1.5 g, 5.3 mmole) was dissolved in chloroform (50 ml), and m-chloroperbenzoic acid (1.3 g, purity 70%, 5.3 mmole) was added to the solution under stirring. After two hours, the reaction mixture was concentrated under reduced pressure. Ethyl acetate (30 ml) wad added to the residue, whereby (E)-7-phenyl-7-(1-oxide-3-pyridyl)-6-heptenoic acid (1.5 g) was obtained as crystals.

EXAMPLE 28

(E)-7-phenyl-7-(3-pyridyl)-6-hepten-1-ol (4 g, 15 mmole) was dissolved in chloroform, and m-chloroperbenzoic acid (3.7 g, purity 70%, 15 mmole) was added to the solution under ice cooling. The mixture was warmed to room temperature and stirred for 1.5 hours. The reaction mixture was concentrated under reduced pressure. The residue was subjected to silica gel column chromatography and eluted with ethyl acetate and then with ethanol-ethyl acetate to give (E)-7-phenyl-7-(1-oxide-3-pyridyl)-6-hepten-1-ol (3.2 g).

By a similar manner to the above Example 27 or 28, compounds (Ie-1–Ie-9) were obtained, whose physical properties are shown in Table 8. Melting points were uncorrected.

What is claimed is:

1. A compound of the structural formula $$(O \leftarrow)N \diagup\!\!\!\diagdown \quad \underset{R^1}{\diagdown}C=CH-(CH_2)_{\overline{n}}R^2$$

wherein

R$^1$ is phenyl, methylenedioxyphenyl or thienyl,

R$^2$ is methyl, hydroxymethyl, nitroxymethyl, formyl, imidazolylmethyl, triazolylmethyl, tetrazolylmethyl, acetal-methyl having 2 to 7 carbon atoms, trialkylsilyloxymethyl having 4 to 10 carbon atoms, C$_{1-3}$alkyl-sulfonyloxymethyl, phenyl-sulfonyloxymethyl, tolylsulfonyloxymethyl, methanesulfonylaminocarbonyloxymethyl, p-toluenesulfonylaminocarbonyloxymethyl, formyloxymethyl, C$_{1-6}$alkyl-carbonyloxymethyl, pyridylcarbonyloxymethyl alkoxycarbonyloxymethyl having 3 to 8 carbon atoms, halogenomethyl, alkoxymethyl having 2 to 5 carbon atoms, aryloxymethyl, cyano, carbamoyl, mono- or di-(C$_{1-6}$)alkyl-aminocarbonyl, mono- or di-arylaminocarbonyl, carbamoyloxymethyl, mono- or di-($_{1-6}$)alkyl-aminocarbonyloxymethyl, mono- or di-aryl-aminocarbonyloxymethyl, thiocarbonyloxymethyl, mono- or di-($_{1-6}$)alkyl-aminothiocarbonyloxymethyl, mono- or di-arylaminothiocarbonyloxymethyl, alkoxycarbonyl having 2 to 5 carbon atoms, carboxyl, wherein the aryl moieties represent phenyl, tolyl, or xylyl, $$(O \leftarrow)N \diagup\!\!\!\diagdown \text{ is } O \leftarrow N \diagup\!\!\!\diagdown \text{ or } N \diagup\!\!\!\diagdown,$$

and n is an integer of 1 to 20, provided that n is 9 to 20 when $$(O \leftarrow)N \diagup\!\!\!\diagdown \text{ is } N \diagup\!\!\!\diagdown$$

and, at the same time R$^2$ is a carboxy or alkoxycarbonyl group, or a pharmaceutically acceptable salt thereof.

2. A compound as claimed in claim 1 wherein $$(O \leftarrow)N \diagup\!\!\!\diagdown \text{ is } N \diagup\!\!\!\diagdown.$$

3. A compound as claimed in claim 1, wherein R$^2$ is methyl, hydroxymethyl, nitroxymethyl, formyl, imidazolylmethyl, triazolylmethyl, tetrazolylmethyl, 2-tetrahydropyranyloxymethyl, 2-tetrahydrofuryloxymethyl, dimethyl-tert-butylsilyloxymethyl, methanesulfonyloxymethyl, p-toluenesulfonyloxymethyl, p-toluenesulfonylaminocarbonyloxymethyl, acetoxymethyl, formyloxymethyl, 3-pyridylcarbonyloxymethyl, iodomethyl, methoxymethyl, phenoxymethyl, cyano, carbamoyl, phenylaminocarbonyl, carbamoyloxymethyl, methylaminocarbonyloxymethyl, n-butylaminocarbonyloxymethyl, phenylaminocarbonyloxymethyl, phenylaminothiocarbonyloxymethyl, methoxycarbonyl.

4. A compound as claimed in claim 1, wherein R$^2$ is hydroxymethyl, a nitroxymethyl group, a carbamoyl group or carbamoyloxymethyl group.

5. A compound as claimed in claim 1, wherein n is an integer of 3 to 9.

6. A compound as claimed in claim 1, wherein the compound is (E)-7-phenyl-7-(3-pyridyl)-6-hepten-1-ol.

7. A compound as claimed in claim 1, wherein the compound is 1-aminocarbonyloxy-(E)-7-phenyl-7-(3-pyridyl)-6-heptene.

8. A compound as claimed in claim 1, wherein the compound is 1-phenylaminocarbonyloxy-(E)-7-phenyl-7-(3-pyridyl)-6-heptene.

9. A compound as claimed in claim 1, wherein the compound is 1-nitroxy-(E)-7-phenyl-7-(3-pyridyl)-6-heptene.

10. A compound as claimed in claim 1, wherein the compound is (E)-7-phenyl-7-(3-pyridyl)-6-heptenamide.

11. A pharmaceutical composition suitable for inhibiting activity of thromboxane A$_2$ synthetase in a mammal, which comprises, as an active ingredient, an effective amount of a compound of the formula

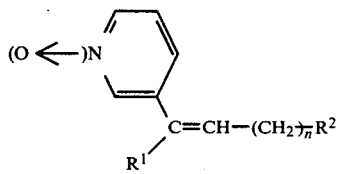

wherein
R¹ is phenyl, methylenedioxyph or thienyl,
R² is methyl, hydroxymethyl, nitroxymethyl, formyl, imidazolylmethyl, triazolylmethyl, tetrazolylmethyl, acetal-methyl having 2 to 7 carbon atoms, trialkylsilyloxymethyl having 4 to 10 carbon atoms, $C_{1-3}$alkyl-sulfonyloxymethyl, phenyl-sulfonyloxymethyl, tolylsulfonyloxymethyl, methanesulfonylaminocarbonyloxymethyl, p-toluenesulfonylaminocarbonyloxymethyl, formyloxymethyl, $C_{1-6}$alkyl-carbonyloxymethyl, pyridylcarbonyloxymethyl, alkoxycarbonyloxymethyl having 3 to 8 carbon atoms, halogenomethyl, alkoxymethyl having 2 to 5 carbon atoms, aryloxymethyl, cyano, carbamoyl, mono- or di-($C_{1-6}$)alkyl-aminocarbonyl, mono- or di-arylaminocarbonyl, carbamoyloxymethyl, mono- or di-($_{1-6}$)alkyl-aminocarbonyloxymethyl, mono- or di-aryl-aminocarbonyloxymethyl, thiocarbonyloxymethyl, mono- or di-($C_{1-6}$)alkyl-aminothiocarbonyloxymethyl, mono- or di-arylaminothiocarbonyloxymethyl, alkoxycarbonyl having 2 to 5 carbon atoms, carboxyl,
wherein the aryl moieties represent phenyl, tolyl, or xylyl,

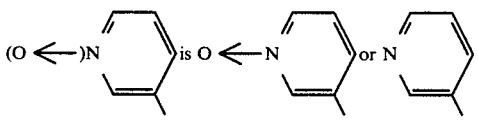

n is an integer of 1 to 20, provided that n is 9 to 20

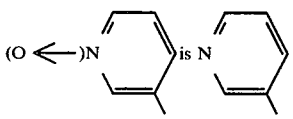

and, at the same time R² is a carboxy or alkoxycarbonyl group, and
a pharmacologically acceptable carrier or excipient thereof.

* * * * *